US012690759B2

(12) United States Patent
Wales et al.

(10) Patent No.: US 12,690,759 B2
(45) Date of Patent: Jul. 28, 2026

(54) TUBING FLOW CONTROL FOR ENDOSCOPIC SYSTEM

(71) Applicant: Boston Scientific Scimed, Inc., Maple Grove, MN (US)

(72) Inventors: Ryan V. Wales, Northborough, MA (US); Sean P. Fleury, Princeton, MA (US); Kurt Nicholas Robakiewicz, Upton, MA (US); Jeff Gray, Sudbury, MA (US); Paul Smith, Smithfield, RI (US); Ryan Vincent William Pollock, Leominster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 258 days.

(21) Appl. No.: 18/340,375

(22) Filed: Jun. 23, 2023

(65) Prior Publication Data

US 2023/0414086 A1     Dec. 28, 2023

Related U.S. Application Data

(60) Provisional application No. 63/355,546, filed on Jun. 24, 2022.

(51) Int. Cl.
| | |
|---|---|
| *A61B 1/12* | (2006.01) |
| *A61B 1/00* | (2006.01) |
| *A61M 39/24* | (2006.01) |

(52) U.S. Cl.
CPC .......... *A61B 1/126* (2013.01); *A61B 1/00119* (2013.01); *A61B 1/00131* (2013.01); *A61M 39/24* (2013.01)

(58) Field of Classification Search
CPC ........................ A61B 1/00119; A61B 1/00131
See application file for complete search history.

(56) References Cited

U.S. PATENT DOCUMENTS

| | | |
|---|---|---|
| 4,971,034 A | 11/1990 | Doi et al. |
| 6,090,094 A | 7/2000 | Clifford et al. |
| | (Continued) | |

FOREIGN PATENT DOCUMENTS

| | | |
|---|---|---|
| CN | 206845973 U | 1/2018 |
| CN | 110859588 A | 3/2020 |
| | (Continued) | |

OTHER PUBLICATIONS

International Search Report and Written Opinion dated Sep. 11, 2023 for International Application No. PCT/US2023/026068.

*Primary Examiner* — Rochelle D Turchen
(74) *Attorney, Agent, or Firm* — Seager, Tufte & Wickhem, LLP

(57) ABSTRACT

Medical devices and methods for using medical devices are disclosed. Example fluid reservoirs and tube sets arranged and configured to couple to an endoscope for use in an endoscopic procedure are disclosed. An example fluid reservoir and tube set includes a fluid reservoir configured to contain a fluid, a fluid supply tube configured to be coupled to the endoscope and having a lumen extending therethrough, wherein the lumen is in fluid communication with the fluid reservoir and a first backflow prevention mechanism coupled to the fluid supply tube, the first backflow prevention mechanism configured to permit fluid to flow through the fluid supply line from the fluid reservoir to the endoscope and to prevent fluid from flowing back through the fluid supply tube from the endoscope to the fluid reservoir.

14 Claims, 19 Drawing Sheets

(56)                     References Cited

U.S. PATENT DOCUMENTS

| | | | |
|---|---|---|---|
| 9,192,284 B2 | 11/2015 | Hirsch et al. | |
| 9,522,017 B2 | 12/2016 | Poll et al. | |
| 11,166,626 B2 | 11/2021 | Roberts | |
| 2006/0229498 A1* | 10/2006 | Kohno | A61B 1/00068 |
| | | | 600/158 |
| 2012/0088974 A1 | 4/2012 | Maurice | |
| 2012/0091092 A1 | 4/2012 | Adams et al. | |
| 2012/0095293 A1 | 4/2012 | Bendele et al. | |
| 2018/0168439 A1* | 6/2018 | Hibbs | A61B 1/126 |
| 2019/0059925 A1* | 2/2019 | Smith | A61B 18/14 |
| 2019/0117046 A1* | 4/2019 | Briggs | A61B 1/126 |
| 2022/0192478 A1 | 6/2022 | Polluck et al. | |

FOREIGN PATENT DOCUMENTS

| | | |
|---|---|---|
| JP | 58-077705 U | 5/1983 |
| JP | S58-177102 U | 11/1983 |
| JP | S59-203539 A | 11/1984 |
| JP | 2003-185301 A | 7/2003 |
| JP | 2009-504302 A | 2/2009 |
| JP | 2013-539716 A | 10/2013 |
| WO | 2007020624 A1 | 2/2007 |

* cited by examiner

TUBING FLOW CONTROL FOR ENDOSCOPIC SYSTEM

CROSS REFERENCE TO RELATED APPLICATIONS

This application claims the benefit of U.S. Provisional Patent Application Ser. No. 63/355,546 filed on Jun. 24, 2022, the disclosure of which is incorporated herein by reference.

TECHNICAL FIELD

This disclosure relates generally to medical fluid containers, tubing assemblies and related methods for fluid delivery, and particularly to tubing and tubing assemblies including a backflow prevention mechanism designed to prevent fluid from backflowing from an endoscope into a fluid reservoir.

BACKGROUND

Conventional endoscope devices have been widely used for performing diagnostic and/or therapeutic treatments. Such endoscope devices may be configured to feed fluid to the end of the endoscope for insufflating the inside of the patient at the target site or washing the lens of the endoscope. For example, lens wash and irrigation fluid provide a liquid such as sterilized water at relatively high pressure to spray across and clear debris from the camera lens or target tissue. The water source for lens wash and irrigation typically includes one or more fluid reservoirs with tubing and cap assemblies that create the plumbing circuit in connection with the endoscope channels and valving to accomplish the desired gas and water functions. Such tubing and cap assemblies are available in various configurations, which typically involve a water bottle, a cap fitted for the specific bottle, and an array of tubing that is extendable through openings in the cap. The tubing typically is arranged to accommodate a specific configuration of endoscope fittings and valving. It is with these considerations in mind that the improvements of the present disclosure may be useful.

SUMMARY

This disclosure provides design, material, manufacturing method, and use alternatives for medical devices. An example fluid reservoir and tube set arranged and configured to couple to an endoscope for use in an endoscopic procedure, the fluid reservoir and tube set includes a fluid reservoir configured to contain a fluid, a fluid supply tube configured to be coupled to the endoscope and having a lumen extending therethrough, wherein the lumen is in fluid communication with the fluid reservoir and a first backflow prevention mechanism coupled to the fluid supply tube, the first backflow prevention mechanism configured to permit fluid to flow through the fluid supply line from the fluid reservoir to the endoscope and to prevent fluid from flowing back through the fluid supply tube from the endoscope to the fluid reservoir.

Alternatively or additionally to any of the embodiments above, wherein the fluid supply tube is configured to permit fluid to flow from the reservoir to a lens of the endoscope.

Alternatively or additionally to any of the embodiments above, wherein the first backflow prevention mechanism includes a portion of the fluid supply tube, wherein the portion of the fluid supply tube is configured to shift between a radially closed configuration and a radially open configuration.

Alternatively or additionally to any of the embodiments above, wherein when in the closed configuration, the portion of the supply tube is configured to prevent fluid from flowing through the fluid supply tube from the endoscope to the reservoir.

Alternatively or additionally to any of the embodiments above, further comprising a gas supply tube, the gas supply tube including a first end and a second end, the first end configured to be coupled to a gas pump, and the second end positioned within the reservoir, and wherein the gas supply tube is configured to permit gas to flow into and pressurize the fluid in the reservoir.

Alternatively or additionally to any of the embodiments above, wherein the portion of the fluid supply tube is configured to shift from the closed configuration to the open configuration in response to the pressurized fluid flowing through the fluid supply tube.

Alternatively or additionally to any of the embodiments above, wherein the portion of the fluid supply tube includes a generally elongate cross-sectional shape in the closed configuration.

Alternatively or additionally to any of the embodiments above wherein the portion of the fluid supply tube includes a generally circular cross-sectional shape in the closed configuration.

Alternatively or additionally to any of the embodiments above, wherein the first backflow prevention mechanism includes an elastic section of material.

Alternatively or additionally to any of the embodiments above, wherein the first backflow prevention mechanism includes a clamp positioned adjacent to the fluid supply tube.

Alternatively or additionally to any of the embodiments above, wherein the clamp is configured to squeeze the fluid supply tube to prevent from flowing back through the fluid supply tube from the endoscope to the fluid reservoir.

Alternatively or additionally to any of the embodiments above, wherein the clamp is configured to open in response to pressurized fluid flowing through the fluid supply tube.

Alternatively or additionally to any of the embodiments above, wherein the clamp is attached to the fluid reservoir.

Alternatively or additionally to any of the embodiments above, further comprising an irrigation supply tube including a first end, a second end, and a lumen extending therethrough, the lumen of the irrigation supply tube being in fluid communication with the fluid reservoir.

Alternatively or additionally to any of the embodiments above, further comprising a second backflow prevention mechanism coupled to the irrigation supply tube, the second backflow prevention mechanism configured to permit fluid to flow through the irrigation supply tube from the fluid reservoir to the endoscope, and to prevent fluid from flowing back through the irrigation supply tube from the endoscope to the fluid reservoir.

Another example fluid reservoir and tube set arranged and configured to couple to an endoscope for use in an endoscopic procedure, the fluid reservoir and tube set includes a fluid reservoir configured to contain a fluid, a fluid supply tube configured to be coupled to the endoscope and having a lumen extending therethrough, wherein the lumen is in fluid communication with the fluid reservoir and a gas supply tube. Further, the gas supply tube includes a first end and a second end, the first end configured to be coupled to a gas pump, the second end of the gas supply tube positioned within the reservoir, wherein the gas supply tube is configured to permit gas to flow into and pressurize the fluid in the reservoir. Additionally, the fluid reservoir and tube set includes a gas flow regulator coupled to the gas supply tube.

Alternatively or additionally to any of the embodiments above, wherein the gas flow regulator is configured to prevent gas from flowing back to the gas pump to maintain a minimum gas pressure in the fluid reservoir.

Alternatively or additionally to any of the embodiments above, wherein the gas flow regulator includes a check valve.

Another fluid reservoir and tube set arranged and configured to couple to an endoscope for use in an endoscopic procedure includes a fluid reservoir configured to contain a fluid, a fluid supply tube configured to be coupled to the endoscope and having a lumen extending therethrough, wherein the lumen is in fluid communication with the fluid reservoir, wherein the lumen of the fluid supply tube is in fluid communication with the fluid reservoir, wherein fluid supply tube includes an undulating region.

Alternatively or additionally to any of the embodiments above, wherein the fluid supply tube folds back on itself to form the undulating region.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

DETAILED DESCRIPTION

Figure 1:
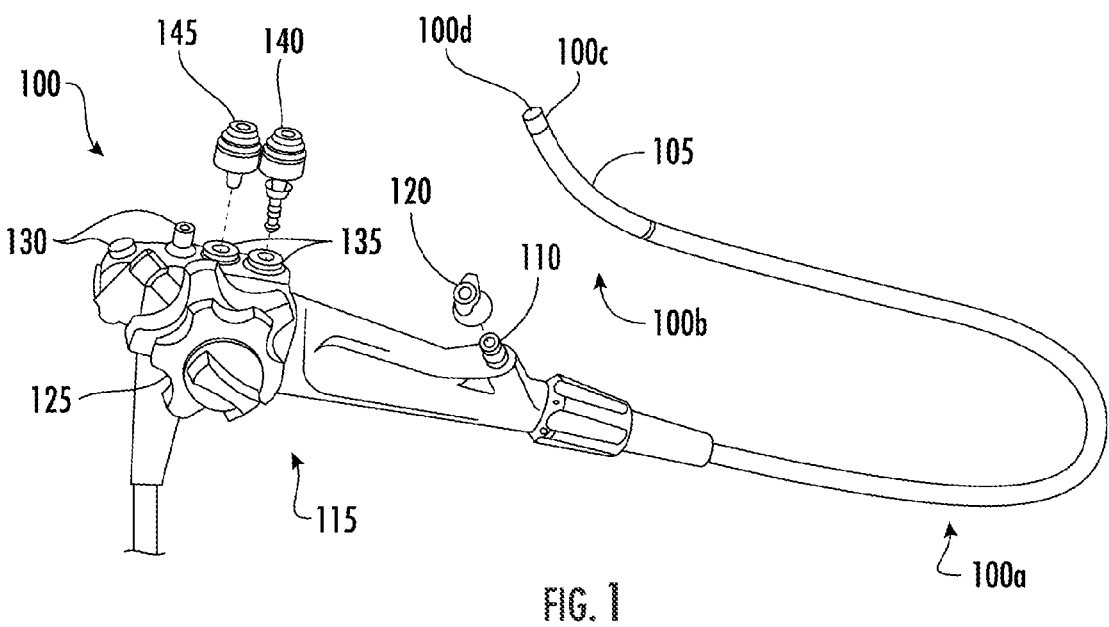
FIG. 1 depicts components of an endoscope.

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, wherein like elements are referred to with the same reference numerals.

Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Although embodiments of the present disclosure are described with specific reference to a bottle (e.g., container, reservoir, or the like) and tube assembly or set, it should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes description of a bottle and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Figure 2:
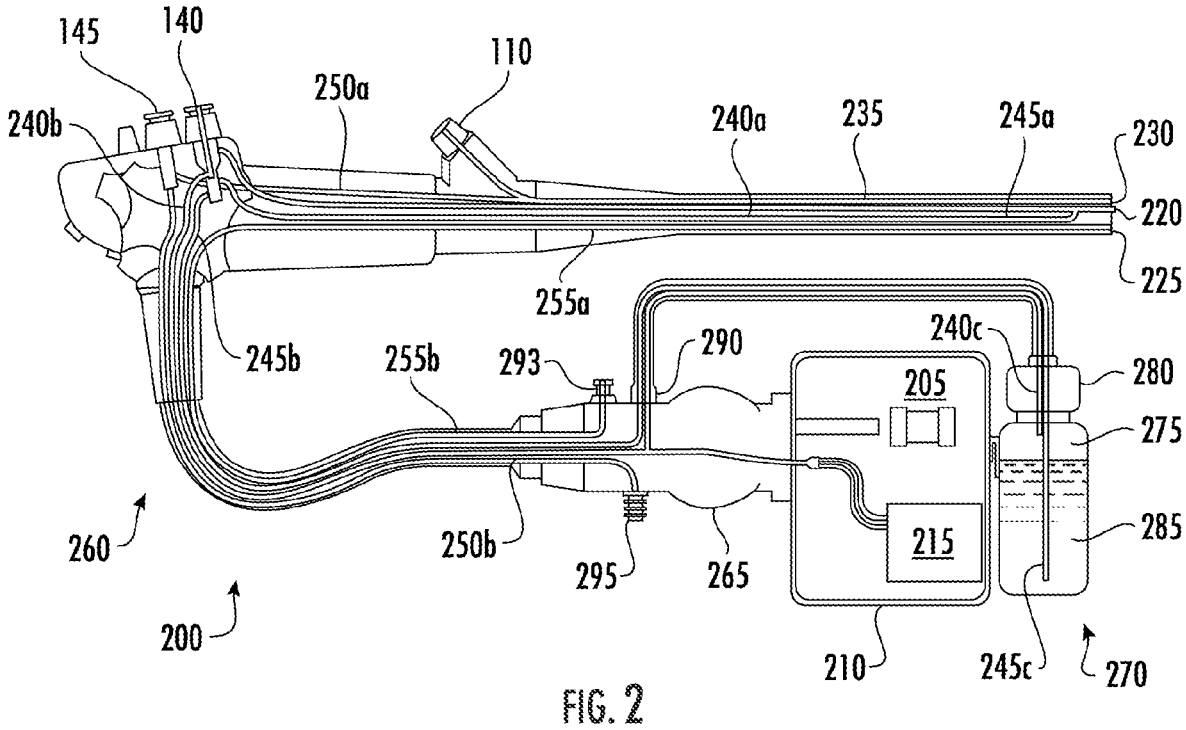
FIG. 2 depicts components of an endoscopic system.

With reference to FIGS. 1-2, an exemplary endoscope 100 and endoscopic system 200 are depicted that may comprise an elongated shaft 100a that is inserted into a patient. A light source 205 feeds illumination light to a distal portion 100b of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air or gas feed pump, in the unit.

The endoscope shaft 100a may include a distal tip 100c provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation fluid to the treatment area of the patient. Illumination windows (not shown) that convey illumination light to the treatment area, and an opening 230 to a working channel 235 extending along the shaft 100a for passing tools to the treatment area, also may be included on the end face 100d of the distal tip 100c. The working channel 235 extends along the shaft 100a to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240a and a lens wash supply line 245a run distally from the gas/water valve 140 along the shaft 100a and converge at the distal tip 100c proximal to the gas/wash nozzle 220 (FIG. 2). The other valve well 135 receives a suction valve 145 for operating a suction operation. A suction supply line 250a runs distally from the suction valve 145 along the shaft 100a to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240b, a lens wash feed line 245b, a suction feed line 250b, an irrigation feed line 255b, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100a to transmit light to the distal tip 100c of the endoscope 100. The connector portion 265 when plugged into the video processing unit 210 also connects the air pump 215 to the gas feed line 240b in the umbilical 260.

A fluid container or reservoir 270 (e.g., water bottle) is fluidly connected to the endoscope 100 through the connector portion 265 and the umbilical 260. A length of gas supply tubing 240c passes from one end positioned in an air gap 275 between the cap 280 (e.g., bottle cap) of the reservoir 270 and the remaining water 285 in the reservoir 270 to a detachable gas/lens wash connection 290 on the outside of the connector portion 265. The gas feed line 240b from the umbilical 260 branches in the connector portion 265 to fluidly communicate with the gas supply tubing 240c at the detachable gas/lens wash connection 290, as well as the air pump 215. A length of lens wash tubing 245c, with one end positioned at the bottom of the reservoir 270, passes through the cap 280 of the reservoir 270 to the same detachable connection 290 as the gas supply tubing 240c on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255b in the umbilical 260. In some embodiments, irrigation water is supplied via a pump (e.g., peristaltic pump) from a water source independent (not shown) from the water reservoir 270. In other embodiments, the irrigation supply tubing and lens wash tubing 245c may source water from the same reservoir. The connector portion 265 may also include a detachable suction connection 295 for suction feed line 250b and suction supply line 250a fluidly connecting a vacuum source (e.g., hospital house suction) (not shown) to the umbilical 260 and endoscope 100.

The gas feed line 240b and lens wash feed line 245b are fluidly connected to the valve well 135 for the gas/water valve 140 and configured such that operation of the gas/water valve in the well controls supply of gas or lens wash to the distal tip 100c of the endoscope 100. The suction feed line 250b is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connection portion 265 and branched to the gas/water valve 140 on the operating handle 115 through the gas feed line 240b in the umbilical 260, as well as through the gas supply tubing 240c to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245c, through the connector portion 265, umbilical 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. As is discussed in greater detail below, outflow check valves, one-way valves, or backflow prevention mechanisms may be placed in the path of the lens wash supply tubing (or other tubing of system 200, 300) to help prevent water from backflowing into the reservoir 270 after the water has passed the valve.

A relatively higher flow rate of irrigation water compared to lens wash is typically required, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the cap of the water source and threaded through the head on the upstream side of the pump. Tubing on the downstream side of the pump is connected to the irrigation feed line 255b in the umbilical 260 and the irrigation supply line 255a endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilical, and down the irrigation supply line in the shaft 100a of the endoscope to the distal tip 100c. In order to equalize the pressure in the water source as water is pumped out of the irrigation supply tubing, an air vent (not shown) may be included in the cap 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves, one-way valves, or backflow prevention mechanisms, similar to the lens wash tubing 245c, may be placed in the path of the irrigation supply tubing to help prevent back-flow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. The hybrid system 300 includes the single water reservoir 305, a cap 310 for the reservoir, gas supply tubing 240c, lens wash supply tubing 245c, irrigation pump 315 with foot switch 318, upstream irrigation tubing 320 and downstream irrigation supply tubing 255c. The cap 310 may be configured to attach in a seal-tight manner to the water reservoir 305 by a typically threaded arrangement. The cap 310 may include a gasket to seal the cap 310 to the reservoir 305. The gasket can be an O-ring, flange, collar, and/or the like and can be formed of any suitable material. A number of through-openings (325a, 325b, 325c) in the cap 310 are provided to receive, respectively, the gas supply tubing 240c, lens wash supply tubing 245c, and upstream irrigation supply tubing 320. In FIGS. 3A-3D, the system depicted includes separate tubing for gas supply, lens wash and irrigation.

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 270, 305, the pressure in the system may be controlled to maintain the lens wash supply tubing 245c at substantially the pressure necessary to accomplish a lower flow rate lens wash, while compensating for reduced pressure in the water reservoir 270, 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240c.

Figures 3A, 3B:
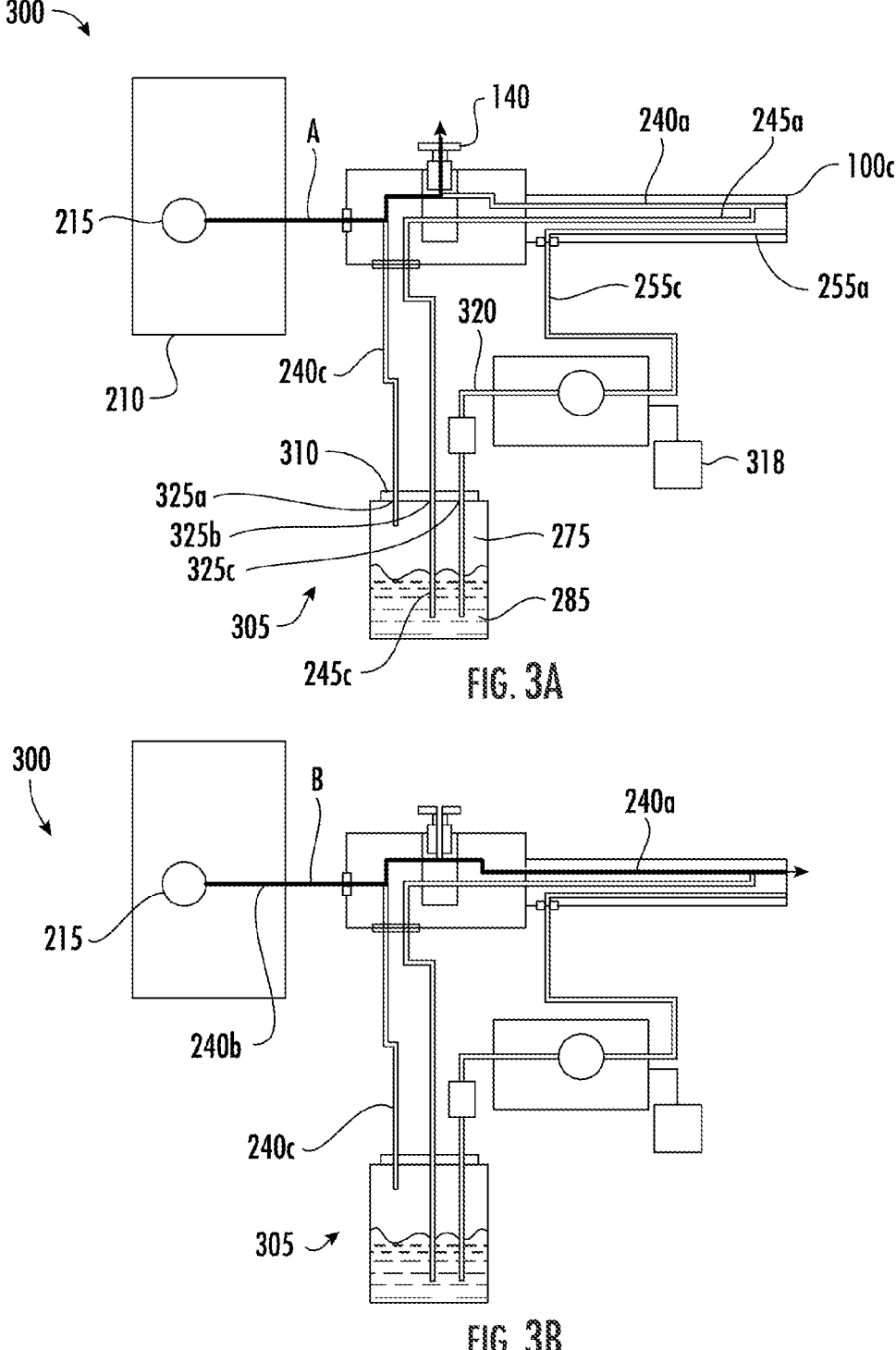
FIG. 3A depicts an endoscopic system wherein the system is activated to deliver air to atmosphere.
FIG. 3B depicts the endoscopic system of FIG. 3A, wherein the system is activated to deliver air to a patient through the patient end of the endoscope.

The schematic set-up in FIGS. 3A-3D has been highlighted to show the different flow paths possible with the hybrid system 300 having supply tubing for irrigation 320 and lens wash 240c connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240b in the umbilical 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 245c.

As shown in FIG. 3B, the endoscope 100 is in a gas delivery state with the gas/water valve 140 in a first position. When gas is called for at the distal tip 100c, for example, to clean the end face 100d of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240b in the umbilical 260 via the connector portion 265. The gas continues through the gas/water valve 140 to the gas supply line 240a in the endoscope shaft 100a and out the gas/lens wash nozzle 220 at the distal tip 100c. There is no build up to pressurize the water reservoir since the system is open at the gas/lens water nozzle 220, and consequently no water is pushed through the lens wash supply tubing 245c.

Figures 3C, 3D:
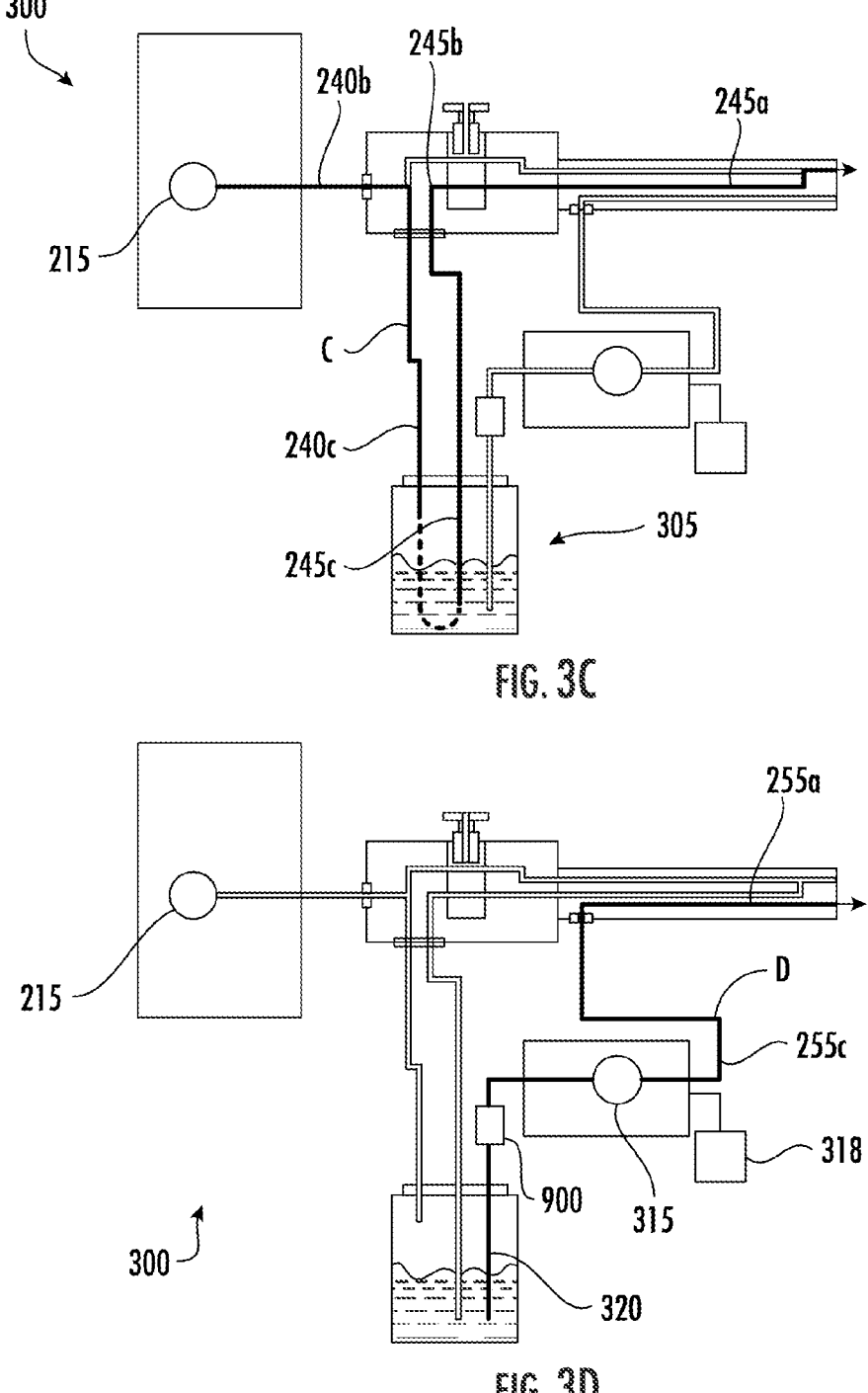
FIG. 3C depicts the endoscopic system of FIG. 3A, wherein the system is activated to deliver lens wash fluid through the patient end of the endoscope.
FIG. 3D depicts the endoscopic system of FIG. 3A, wherein the system is activated to deliver irrigation fluid through the patient end of the endoscope.

As shown in FIG. 3C, the endoscope 100 is in a lens wash delivery state with the gas/water valve 140 in a second position. When lens wash is called for at the distal tip 100c, for example, to clean the end face 100d of the distal tip 100c, the user, keeping the vent hole in the air/water valve closed off, depresses the valve 140 to its furthest point in the valve well 135. The second position blocks off the gas supply to both atmosphere and the gas supply line 240a in the endoscope, and opens up the gas/water valve 140 to allow lens wash water to pass through to the lens wash supply line 245a in the endoscope shaft 100a and out the gas/lens wash nozzle 220 at the distal tip 100c. In this state, gas (pressure) is delivered along path C from the air pump 215, through the branched line in the connector portion 265 and out of the gas supply tubing 240c to the water reservoir 305. The gas (pressure) pressurizes the surface of the remaining water 285 in the reservoir 305 and pushes water up the lens wash supply tube 245c to the connector portion 265. The pressurized lens wash water is pushed further through the lens wash feed line 245b in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

As shown in FIG. 3D, the endoscope 100 is in an irrigation delivery state. This may be performed at the same or a different time from the delivery of gas and/or lens wash. When irrigation is called for at the distal tip 100c, for example, if visibility in the treatment area is poor or blocked by debris, or the like, the user activates the irrigation pump 315 (e.g., by depressing foot switch 318) to delivery water along path D. With the pump 315 activated, water is sucked out of the water reservoir 305 through the upstream irrigation supply tubing 320 and pumped along the downstream irrigation supply tubing 255c to the connector portion 265. The irrigation pump head pressure pushes the irrigation water further through the irrigation feed line 255b in the umbilical 260, through the irrigation supply line 255a in the endoscope shaft 100a, and out the irrigation opening 225 at the distal tip 100c. The irrigation pump pressure may be calibrated, along with the endoscope irrigation feed and supply lines and external tubing, to deliver a certain range of flow rate of the irrigation fluid.

In some embodiments, a variety of backflow prevention mechanisms may be incorporated into the embodiments disclosed herein, including the tubing of the system 200, 300. For example, different backflow prevention mechanisms (e.g., clamp mechanisms, valves, compressible tubing, traps, etc.) may be incorporated in the lens wash supply tubing 245c, upstream irrigation supply tubing 320, and/or downstream irrigation supply tubing 255c to help prevent backflow of water from either or both of the lens wash and irrigation tubing in the event of a negative pressure situation.

Figure 4:
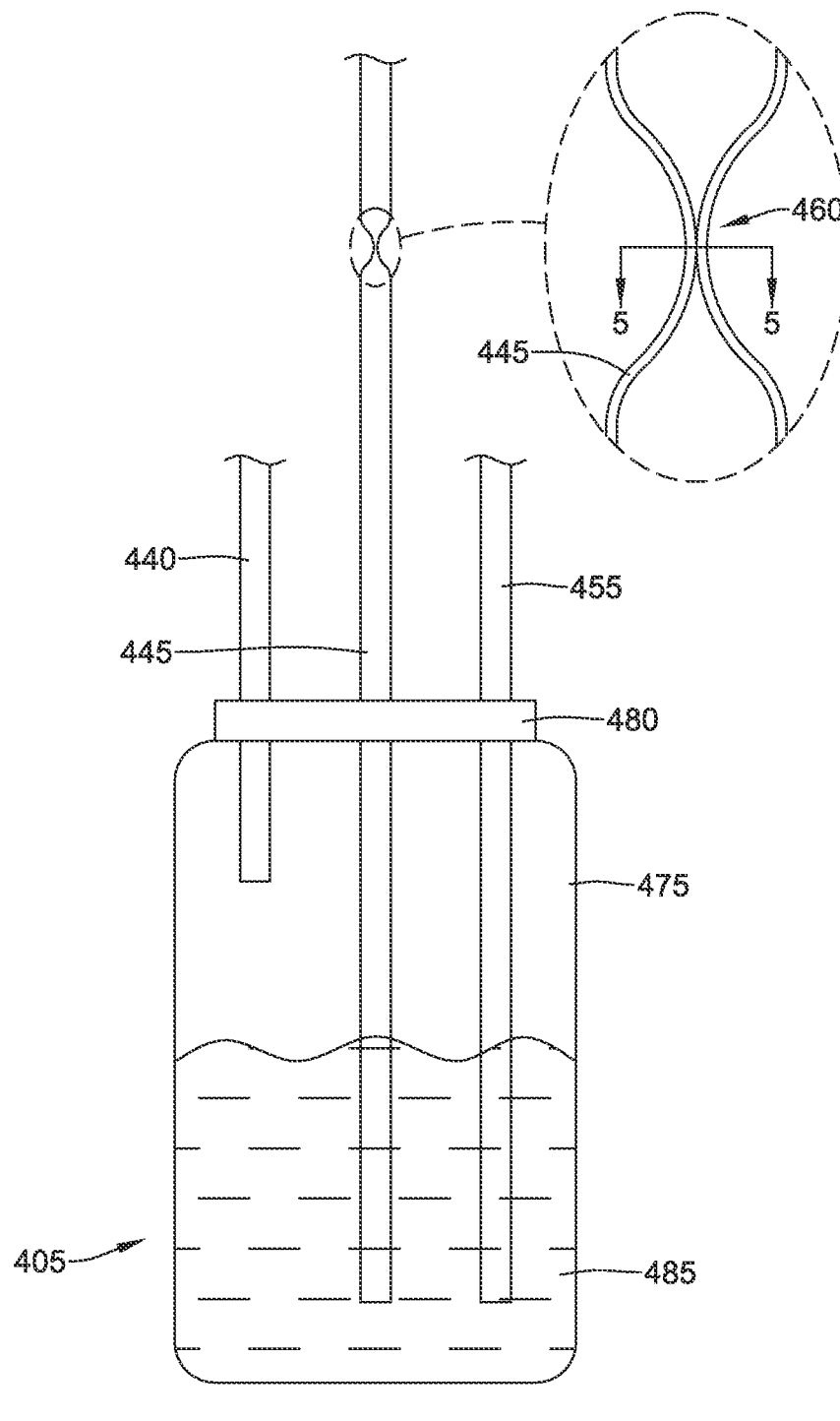
FIG. 4 depicts a portion of an endoscopic system including a container and a plurality of tubes coupled thereto.

FIG. 4 illustrates an example fluid reservoir 405 (e.g., water container). The fluid reservoir 405 may be similar in form and function to the water reservoirs 270, 305 of the endoscopic systems 200, 300, described herein. For example, FIG. 4 illustrates that the water reservoir 405 may include an inner chamber designed to hold varying volumes of water 485. Additionally, FIG. 4 illustrates a cap 480 may be securely fastened to the water reservoir 405. Securement of the cap 480 to the water reservoir 405 may establish an air gap 475 between the cap 480 of the reservoir 405 and the water 485 in the reservoir 405.

FIG. 4 further illustrates a length of gas supply tubing 440 passing from one end positioned in an air gap 475 and through an opening in the cap 480 of the reservoir 405. It can be appreciated from FIG. 4 that the gas supply tubing 440 may be similar in form and function to the gas supply tubing 240c described herein. Additionally, FIG. 4 illustrates a length of lens wash tubing 445 having one end positioned within the water 485 of the reservoir 405 and passing through an opening in the cap 480 of the reservoir 405. It can be appreciated from FIG. 4 that the lens wash tubing 445 may be similar in form and function to the lens wash tubing 245c described herein. FIG. 4 further illustrates a length of irrigation tubing 455 having one end positioned within the water 485 of the reservoir 405 and passing through an opening in the cap 480 of the reservoir 405. It can be appreciated from FIG. 4 that the irrigation tubing 455 may be similar in form and function to the irrigation tubing 320 described herein. While FIG. 4 illustrates that the irrigation supply tubing 455 and lens wash tubing 445 may source water from the same reservoir 405, in some embodiments the irrigation water may be supplied via a pump (e.g., peristaltic pump) from a water source independent (not shown) from the water reservoir 405.

The utilization of insufflation, irrigation and lens wash to provide a clear view of the working lumen 235 and the target tissue may generate a vacuum in one or more of the working channel 235, the gas supply tubing 440, the lens wash supply tubing 445 and/or the irrigation feed tubing 455. The creation of a vacuum in one or more of the working channel 235, the gas supply tubing 440, the lens wash supply tubing 445 and/or the irrigation feed tubing 455 may potentially create a negative pressure that pulls fluids from a patient's body lumen back through the endoscope and into one or more of the working channel 235, the gas supply tubing 440, the lens wash supply tubing 445, and the fluid reservoir 405, thereby contaminating the clean water located in the lumens of the endoscope 100 and the fluid reservoir 405.

Accordingly, in some embodiments the working channel 235, the gas supply tubing 440, the lens wash supply tubing 445 and the irrigation feed tubing 455 may include a feature which is designed to prevent fluid from flowing from outside the distal tip 100c of the endoscope 100 back through the working channel 235, the gas supply tubing 440, the lens wash supply tubing 445 or the irrigation feed tubing 455 and into the fluid reservoir 405. For example, the detailed view of FIG. 4 illustrates that, in some embodiments, a portion of the lens wash tubing 445 may include a feature which is designed to prevent fluid from flowing from outside the distal tip 100c of the endoscope 100 back through the working channel 235, the gas supply tubing 440, the lens wash supply tubing 445 and/or the irrigation feed tubing 455 and into the fluid reservoir 405. Including a mechanism designed for fluid backflow prevention may be beneficial because it may reduce the possibility of cross-contamination of fluid between patients.

The detailed view of FIG. 4 illustrates that, in some embodiments, the lens wash tubing 445 may include a region of tubing 460 which is laterally or radially closed (e.g., radially collapsed) in its native state. In this configuration, the inner surface of the lens wash tubing 445 along the region of tubing 460 may close radially inward such that it contacts itself, thereby forming a fluid tight seal designed to prevent fluid located upstream from the radially closed region 460 from flowing back into the fluid reservoir 405. The detailed view of FIG. 4 illustrates that the radially closed region of tubing 460 may extend along a length of the lens wash tubing 445.

Figure 5A:
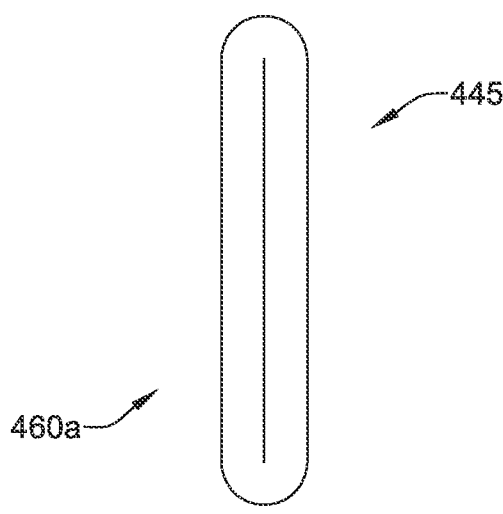
FIG. 5A depicts a cross-sectional view of a tube of FIG. 4 taken along line 5-5.
Figure 5B:
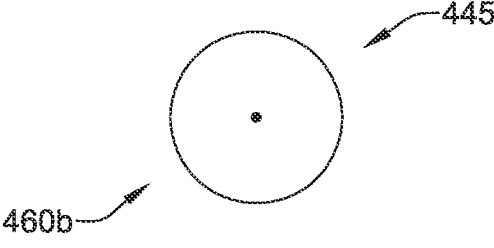
FIG. 5B depicts another cross-sectional view of a tube of FIG. 4 taken along line 5-5.

In some examples, the collapsed region of tubing 460 may be designed to include cross-sections having different shapes. For example, FIGS. 5A and 5B illustrate the two embodiments of a cross-sectional shape of the region 460 taken along line 5-5 of FIG. 4. As illustrated in FIG. 5A, in some examples, the cross-sectional shape of the closed region of tubing 460 (in its collapsed state) may be generally elongate or ovular. FIG. 5B illustrates that, in other examples, the cross-sectional shape of the collapsed region 460 taken along 5-5 of FIG. 4 may be generally circular. It can be appreciated that both FIG. 5A and FIG. 5B illustrate that that the inner surface of the lens wash tubing 445 may close upon itself (e.g., radially collapse) to provide a fluid tight seal designed to prevent fluid from backflowing from a position upstream the tubing region 460 to a position downstream of the tubing region 460 (e.g., into the water reservoir 405).

Additionally, in some examples the collapsed region 460 of the lens wash tubing 445 may include cross-sectional shapes other than generally ovular and circular. For example, the collapsed region 460 of the lens wash tubing 445 may include a cross-sectional shape that is generally elliptical, triangular, square, half-moon, polygonal, rectangular, star-shaped, etc.

In some examples, the region of tubing 460 may be designed to radially expand to permit fluid 485 to flow from the water reservoir 405 upstream to the operating handle 115 and eventually through elongated sheath 100a of the endoscope 100. As discussed herein, in is native state (or in a first position), the region of tubing 460 of the lens wash tubing 445 may be designed to be radially closed such that a column of water present in the lens wash line upstream of the region of tubing 460 is not strong enough to radially expand region of tubing 460 (thereby preventing fluid from flowing backward through closed region 460 and into the water reservoir 460).

Figure 6:
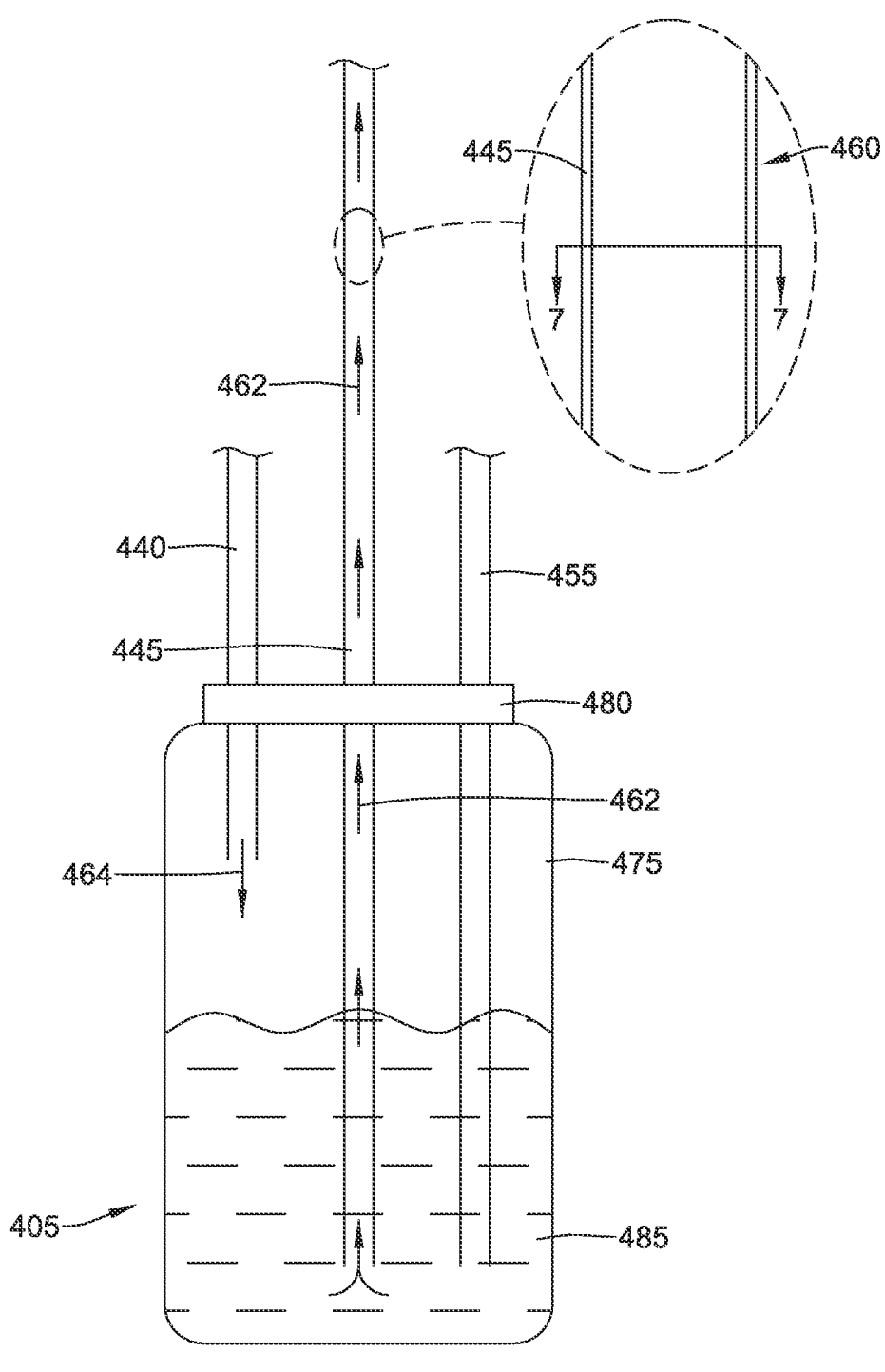
FIG. 6 depicts the container and the plurality of tubes of FIG. 4, whereby gas and fluid are passing through one or more tubes.

However, in some examples, the radially collapsed region of tubing 460 may be designed to radially expand in the presence of water 485 being forced upstream through the lens wash tubing 445. For example, FIG. 6 illustrates water 485 being pressurized via the introduction of gas into the water reservoir 405 through the gas supply tubing 440. Referring back to the system configuration described with respect to FIG. 3C, when the endoscopic system 300 is in a lens wash delivery configuration, gas (pressure) may be delivered from the air pump 215 and out of the gas supply tubing 440 to the water reservoir 405. In FIG. 6, the gas entering the reservoir is depicted by the arrow 464. The gas (pressure) pressurizes the surface of the water 485 in the reservoir 405 and pushes water up the lens wash supply tube 445. The pressurized lens wash water is pushed through the lens wash supply tube 445 to the endoscope 100. FIG. 6 illustrates that if the gas pressure delivered by the air pump meets a given threshold, the fluid flowing through the lens was supply tube 445 will generate sufficient pressure (the water 485 flowing upstream through the lens wash tubing 445 is depicted by the arrows 462) to force the region of tubing 460 to expand radially outward (as illustrated in the detailed view of FIG. 6), thereby permitting the water 485 to flow upstream past the tubing region 460 and to the endoscope 100.

Figure 7:
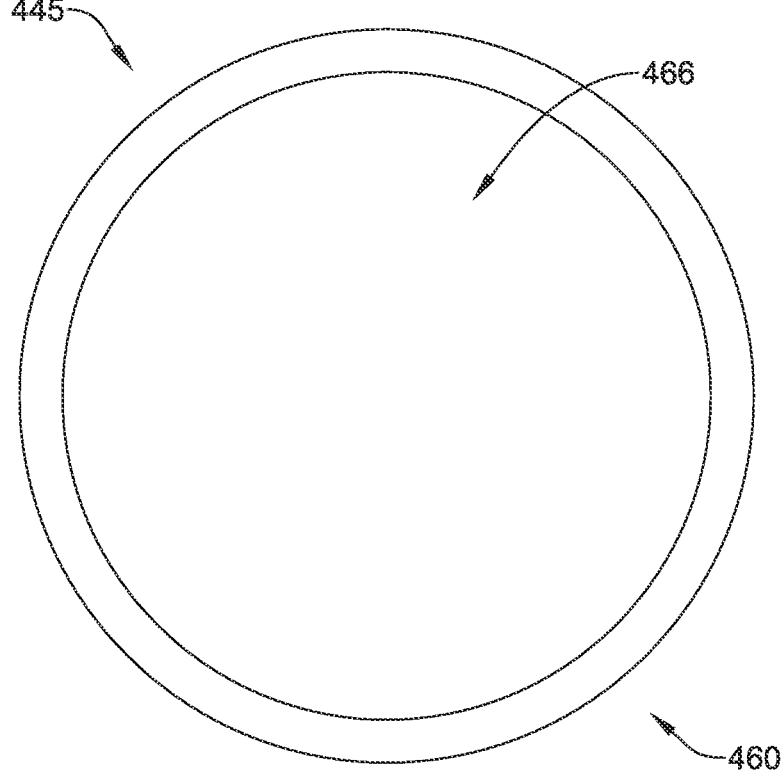
FIG. 7 depicts a cross-sectional view of a tube of FIG. 6 taken along line 7-7.

FIG. 7 illustrates a cross-sectional view of the lens wash tubing 445 taken along line 7-7 of FIG. 6. Comparing the cross-sectional view of the lens wash tubing 445 shown in FIG. 7 (in a radially expanded state) to the cross-sectional views of the lens wash tubing shown in FIGS. 5A and 5B (in a radially collapsed state), illustrates that in a radially expanded state, the inner wall of the lens wash tubing 445 along the region of tubing 460 has expanded away from itself in FIG. 7 (e.g., the tube 445 has been forced open by a sufficient fluid flow), thereby permitting the water 485 to flow upstream through the open lumen 466 of the lens wash tubing 445.

However, as described herein, the flow of water for lens wash may be stopped by a user releasing the gas/water valve 140 from a depressed position on the operating handle 115 of the endoscope 100. After the gas/water valve 140 is released and the gas stops flowing into the water reservoir 405, the fluid pressure expanding the collapsed tubing region 460 of the lens wash tubing 445 may decrease and thereby permit the tubing region 460 to collapse to a position in which the inner surface of the lens tubing 445 seals upon itself and prevents fluid upstream of the tubing region 460 to flow back into the water reservoir 460.

The material which is utilized to construct the portion of the lens wash tubing 445 defining the radially collapsible tubing region 460 may be selected based on its radial elasticity and the corresponding force required to radially expand the tubing from a collapsed state to an expanded state. The material which is utilized to construct the portion of the lens wash tubing 445 may be elastic. For example, the material selected construct the radially collapsible tubing region 460 may be selected based on its ability to effectively prevent the backflow of fluid when fluid positioned upstream of the tubing region 460 is in a static state, yet the material of the tubing region 460 must also be able to radially expand when the gas (pressure) delivered from the air pump 215 generates a given upstream fluid flow and corresponding outward radial force through the lens wash tubing 445.

Figure 8:
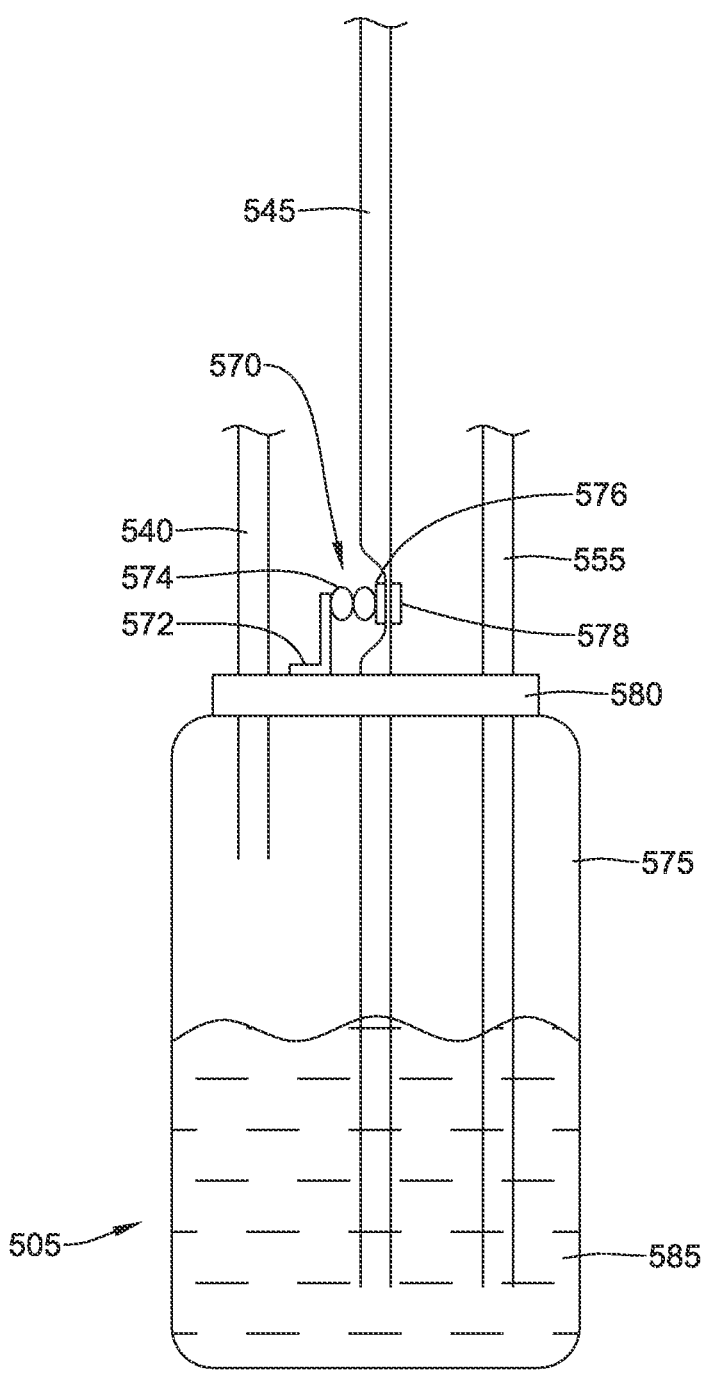
FIG. 8 depicts a portion of another endoscope system including a container and a plurality of tubes coupled thereto.
Figure 9:
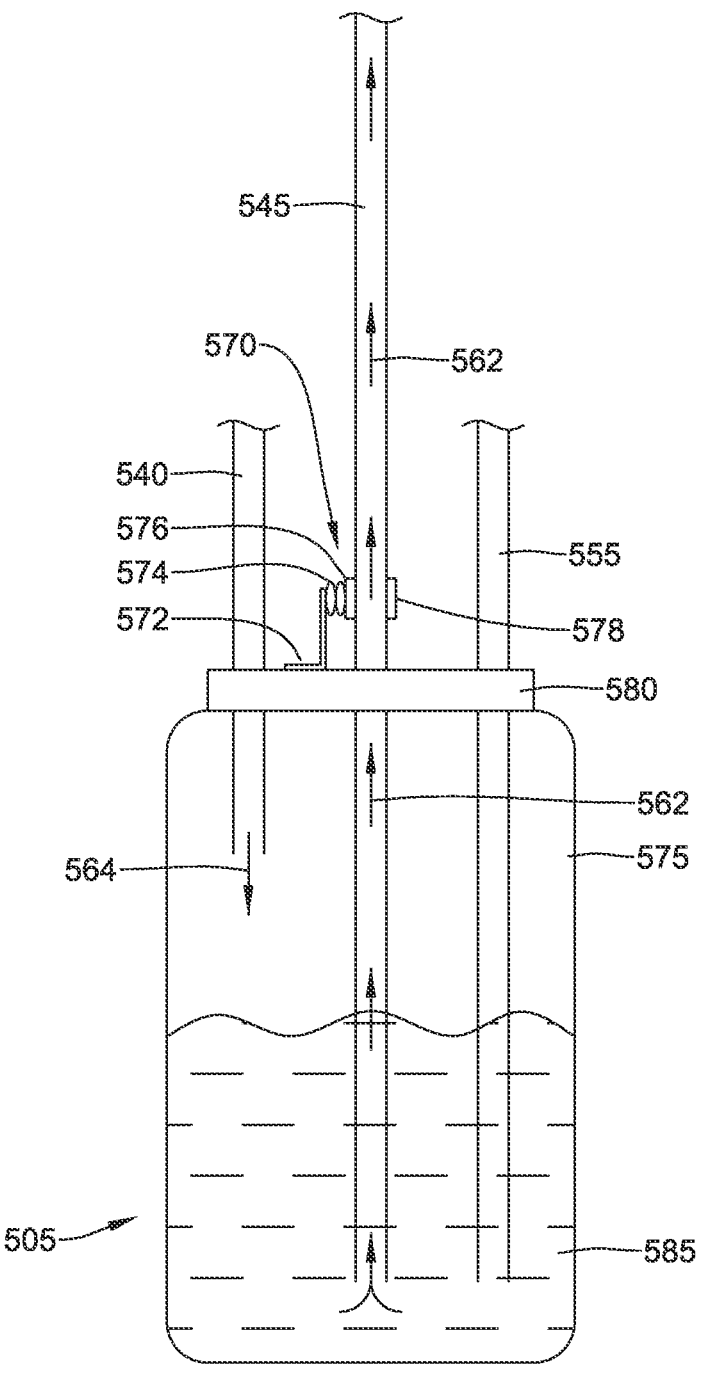
FIG. 9 depicts the container and the plurality of tubes of FIG. 8, whereby gas and fluid are passing through one or more tubes.

FIGS. 8-9 illustrate another backflow prevention mechanism which may be incorporated in the lens wash supply tubing 245c, upstream irrigation supply tubing 320, and/or downstream irrigation supply tubing 255c to help prevent backflow of water from either or both of the lens wash and irrigation tubing in the event of a negative pressure situation.

FIG. 8 illustrates an example water reservoir (e.g., container) 505. The water reservoir 505 may be similar in form and function to the water reservoirs 270, 305 of the systems 200, 300, described herein. For example, FIG. 8 illustrates that the water reservoir 505 may include an inner chamber designed to hold varying volumes of water 585. Additionally, FIG. 8 illustrates a cap 580 (e.g., a bottle cap) may be securely fastened to the water reservoir 505. Securement of the cap 580 to the water reservoir 505 may establish an air gap 575 between the cap 580 of the reservoir 505 and the water 585 in the reservoir 505.

FIG. 8 further illustrates a length of gas supply tubing 540 passing from one end positioned in an air gap 575 and through an opening in the cap 580 of the reservoir 505. It can be appreciated from FIG. 8 that the gas supply tubing 540 may be similar in form and function to the gas supply tubing 240c described herein. Additionally, FIG. 8 illustrates a length of lens wash tubing 545 having one end positioned within the water 585 of the reservoir 505 and passing through an opening in the cap 580 of the reservoir 505. It can be appreciated from FIG. 8 that the lens wash tubing 545 may be similar in form and function to the lens wash tubing 245c described herein. FIG. 8 further illustrates a length of irrigation tubing 555 having one end positioned within the water 585 of the reservoir 505 and passing through an opening in the cap 580 of the reservoir 505. It can be appreciated from FIG. 8 that the irrigation tubing 555 may be similar in form and function to the irrigation tubing 320 described herein. While FIG. 8 illustrates that the irrigation supply tubing 555 and lens wash tubing 545 may source water from the same reservoir 505, in some embodiments the irrigation water may be supplied via a pump (e.g., peristaltic pump) from a water source independent (not shown) from the water reservoir 505.

FIG. 8 further illustrates that endoscopic systems 200, 300 may include a clamp mechanism 570 secured to the cap 580. The clamp mechanism 570 may include a bracket 572 which extends in a vertical direction from the cap 580 and may also include a lateral beam portion 578 which extends laterally from the vertical portion and wraps around the outer surface of the lens wash tubing 545. Additionally, the clamp mechanism 570 may further include a pad 576 attached to the distal end of a spring 574. FIG. 8 further illustrates that the proximal end of the spring 574 may be attached to the vertically extending portion of the bracket 572.

FIG. 8 further illustrates the lens wash tubing 545 positioned between the pad 576 and the lateral beam portion 578 of the bracket 572. Additionally, FIG. 8 illustrates a state in which the lens wash is not being activated and therefore no pressure is being passed from the gas supply tubing 540 into the water reservoir 505 to force water 585 upstream through the lens wash tubing 545. Accordingly, FIG. 8 illustrates that the spring 547 has sufficient force to expand and pinch (e.g., squeeze, press, etc.) the lens wash tubing 545 between the pad 576 and the lateral beam portion 578 of the bracket 572 such that the inner luminal surface of the lens wash tubing 545 contacts itself, thereby closing the inner lumen of the lens wash tubing 545 and preventing static fluid present in the lens wash tubing 545 from flowing back into the reservoir 505.

FIG. 9 illustrates that the lens wash tubing 545 may be designed to radially expand in the presence of water 585 being pushed upstream through the lens wash tubing 545. For example, FIG. 9 illustrates water 585 being pressurized via the introduction of gas into the water reservoir 505 through the gas supply tubing 540. Referring back to the system configuration described with respect to FIG. 3C, when the endoscopic system 300 is in a lens wash delivery configuration, gas (pressure) may be delivered from the air pump 215 and out of the gas supply tubing 540 to the water reservoir 505. In FIG. 9, the gas entering the reservoir 505 is depicted by the arrow 564. The gas (pressure) pressurizes the surface of the water 585 in the reservoir 505 and pushes water up the lens wash supply tube 545. The pressurized lens wash water 585 is pushed through the lens wash supply tube 545 to the endoscope 100. FIG. 9 illustrates that if the gas pressure delivered by the air pump meets a given threshold, the fluid flowing through the lens was supply tube 545 will generate sufficient pressure (the water 585 flowing upstream through the lens wash tubing 545 is depicted by the arrows 562) to force the region of tubing 560 to overcome the force of the spring 574 and expand radially outward (as illustrated in FIG. 9), thereby permitting the water 585 to flow upstream past the clamp mechanism 570 and to the endoscope 100.

Figure 10:
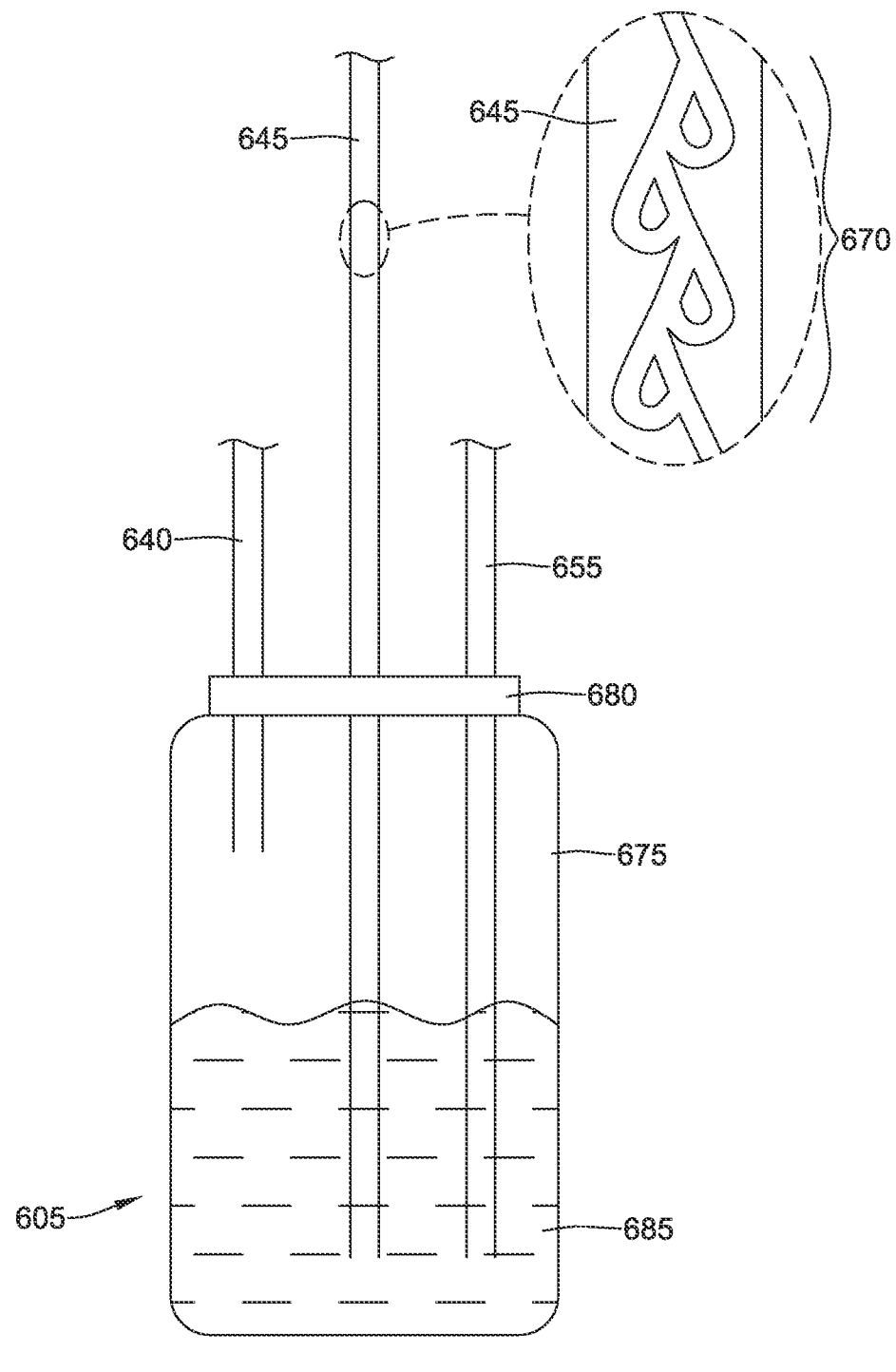
FIG. 10 depicts a portion of another endoscopic system including a container and a plurality of tubes coupled thereto, whereby one of the tubes includes a Tesla valve.
Figure 11A:
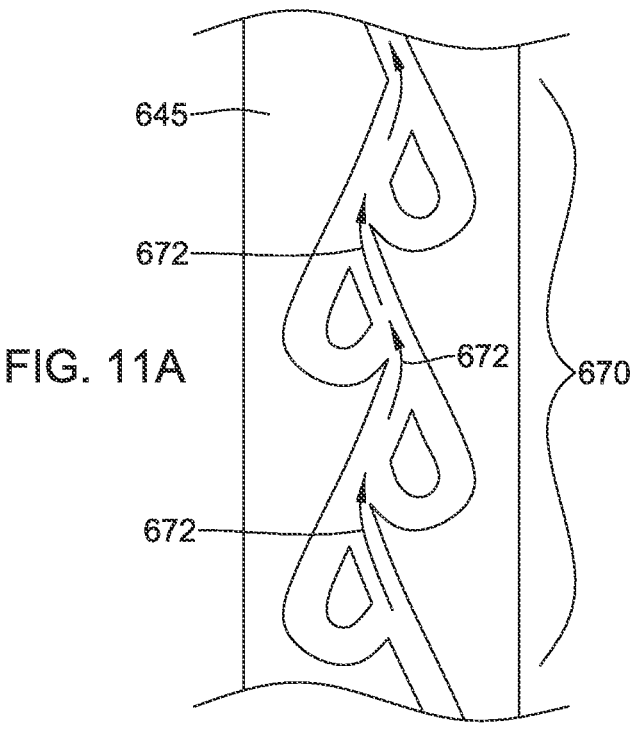
FIG. 11A depicts fluid flowing through the Tesla valve of the tube of FIG. 10.
Figure 11B:
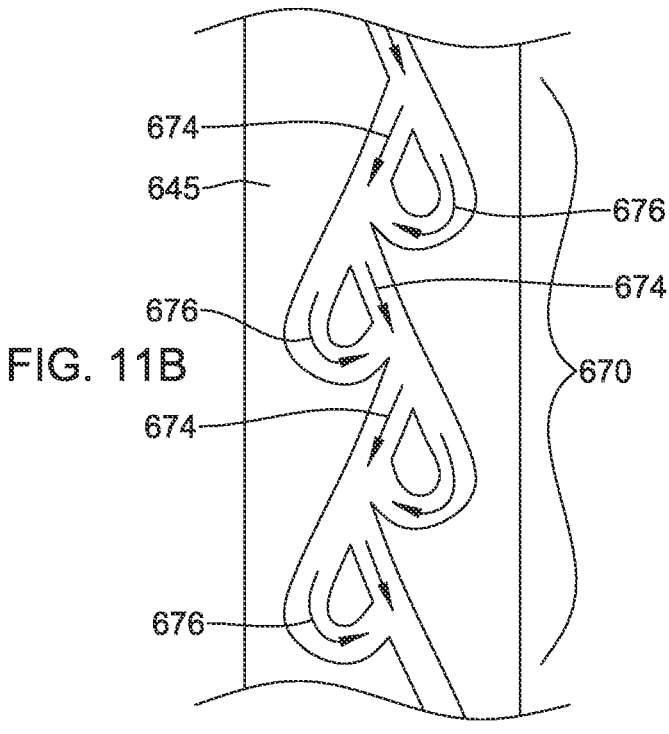
FIG. 11B depicts fluid being prevented from flowing back through the Tesla valve of the tube of FIG. 10.

FIGS. 10-11B illustrate another backflow prevention mechanism which may be incorporated in the lens wash supply tubing 245c, upstream irrigation supply tubing 320, and/or downstream irrigation supply tubing 255c to help prevent backflow of water from either or both of the lens wash and irrigation tubing in the event of a negative pressure situation.

FIG. 10 illustrates an example water reservoir (e.g., container) 605. The water reservoir 605 may be similar in form and function to the water reservoirs 270, 305 of the systems 200, 300, described herein. For example, FIG. 10 illustrates that the water reservoir 605 may include an inner chamber designed to hold varying volumes of water 685. Additionally, FIG. 10 illustrates a cap 680 (e.g., a bottle cap) may be securely fastened to the water reservoir 605. Securement of the cap 680 to the water reservoir 605 may establish an air gap 675 between the cap of the reservoir 605 and the water 685 in the reservoir 605.

FIG. 10 further illustrates a length of gas supply tubing 640 passing from one end positioned in an air gap 675 and through an opening in the cap 680 of the reservoir 605. It can be appreciated from FIG. 10 that the gas supply tubing 640 may be similar in form and function to the gas supply tubing 240c described herein. Additionally, FIG. 10 illustrates a length of lens wash tubing 645 having one end positioned within the water 685 of the reservoir 605 and passing through an opening in the cap 680 of the reservoir 605. It can be appreciated from FIG. 10 that the lens wash tubing 645 may be similar in form and function to the lens wash tubing 245c described herein. FIG. 10 further illustrates a length of irrigation tubing 655 having one end positioned within the water 685 of the reservoir 605 and passing through an opening in the cap 680 of the reservoir 605. It can be appreciated from FIG. 10 that the irrigation tubing 655 may be similar in form and function to the irrigation tubing 320 described herein. While FIG. 10 illustrates that the irrigation supply tubing 655 and lens wash tubing 645 may source water from the same reservoir 605, in some embodiments the irrigation water may be supplied via a pump (e.g., peristaltic pump) from a water source independent (not shown) from the water reservoir 605.

The detailed view of FIG. 10 further illustrates that a portion of the lens wash tubing 645 of the endoscopic systems 200, 300 may include a Tesla valve 670. Generally, a Tesla valve can be described as a fixed-geometry passive check valve whose geometry permits fluid to flow preferentially in only one direction. In other words, the Tesla valve 670 illustrated in the detailed view of FIG. 10 may include enlargements, recesses, projections, baffles, or buckets which formed within the lumen of the lens wash tubing 445 which permit water 685 to pass relatively unimpeded upstream from the reservoir 605 toward the endoscope 100, yet also resists the backflow of fluid in the opposite direction (e.g., prevents the backflow of fluid from the endoscope toward the reservoir 605).

FIG. 11A illustrates the unimpeded passage of water 685 through the Tesla valve 670 described with respect to FIG. 10. As depicted by the arrows 672 in FIG. 11A, the water 685 from the reservoir 605 is permitted to flow with virtually no resistance in an upstream direction through the Tesla valve 670. However, FIG. 11B illustrates that fluid attempting to flow in a downstream direction (the fluid attempting to flow in a downstream direction are depicted by the arrows 674), is repeatedly blocked by fluid flowing through multiple interfering flow paths 676.

Figure 12:
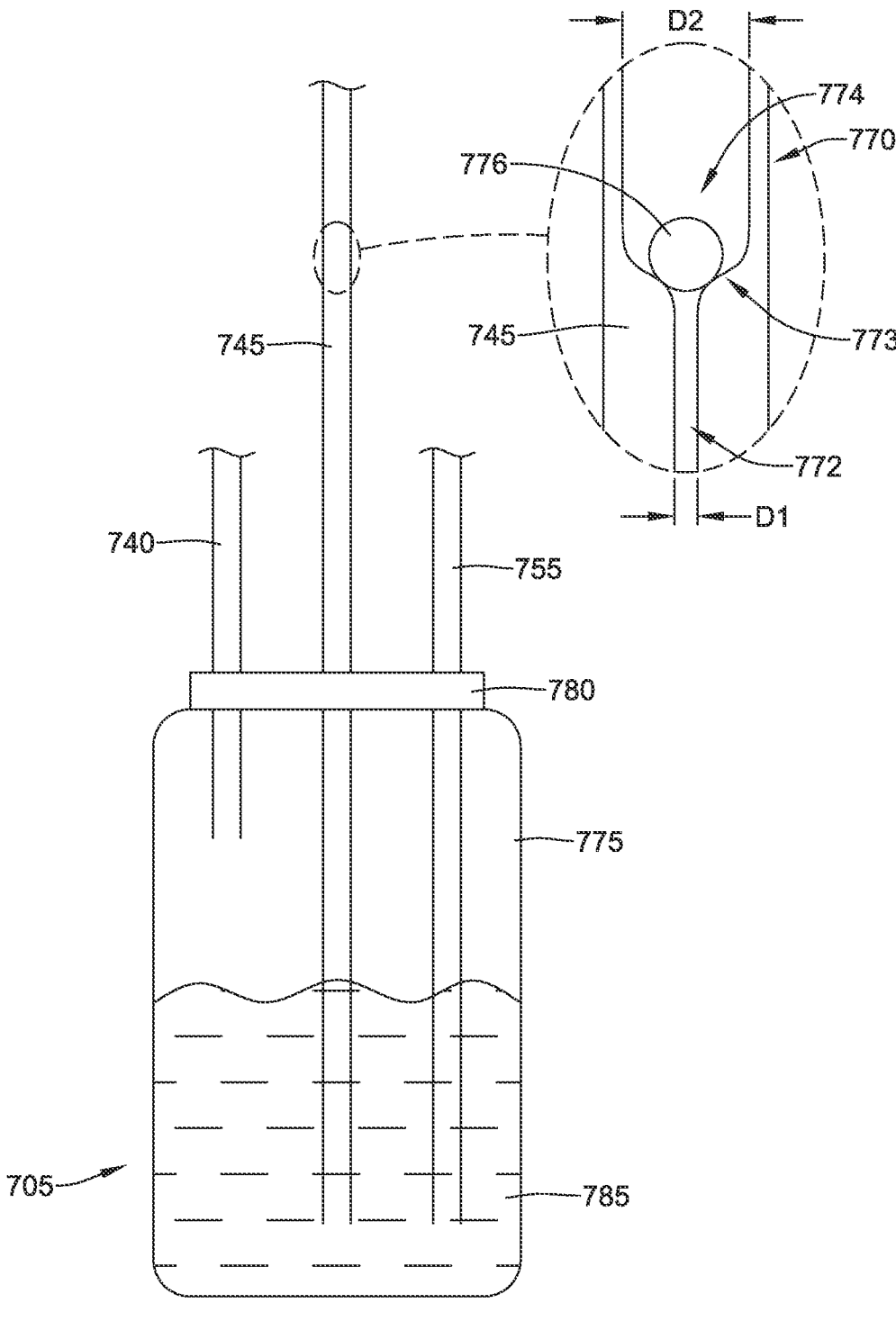
FIG. 12 depicts a portion of another endoscopic system including a container and a plurality of tubes coupled thereto.
Figure 13:
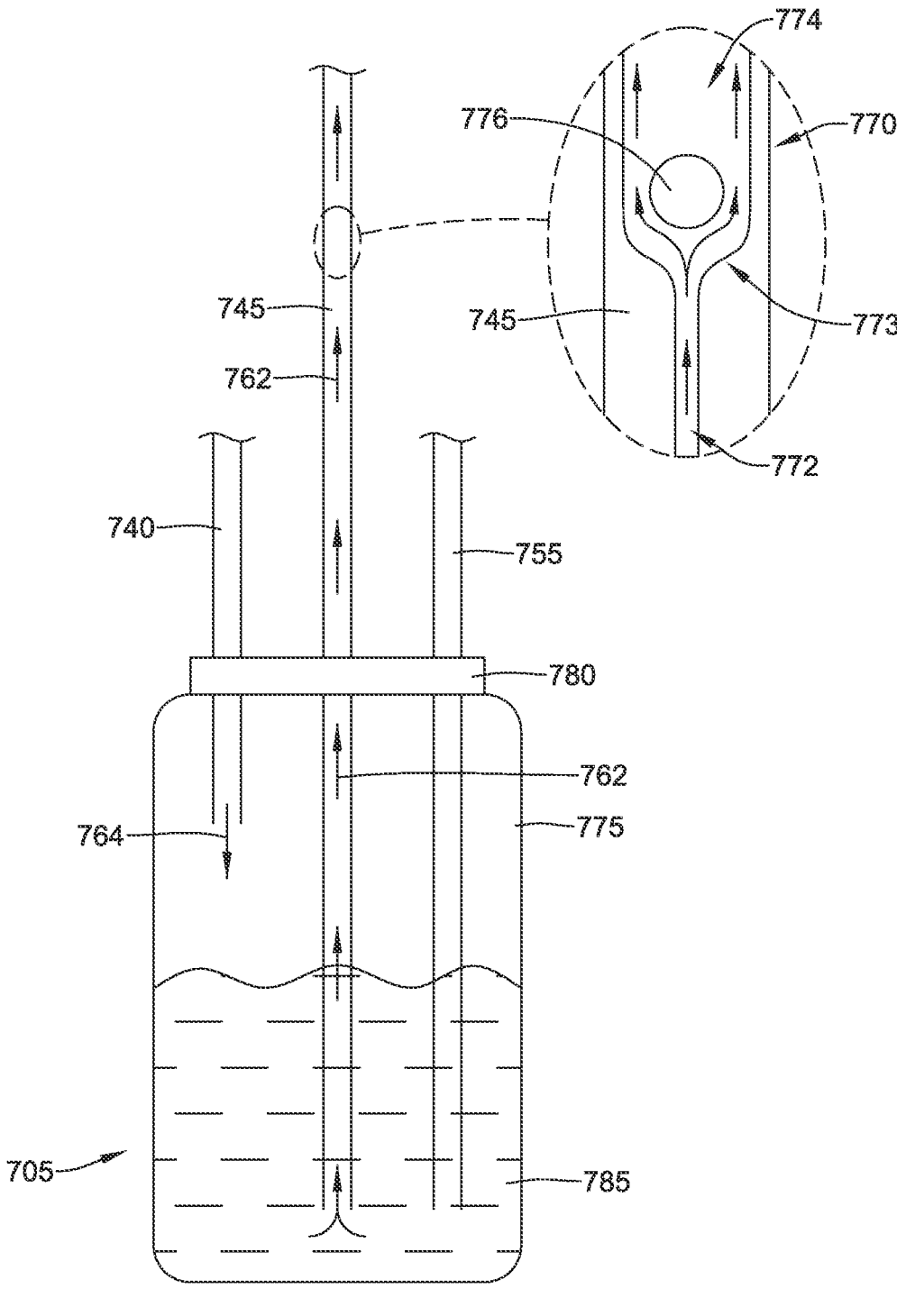
FIG. 13 depicts the container and the plurality of tubes of FIG. 12, whereby gas and fluid are passing through one or more tubes.

FIGS. 12-13 illustrate another backflow prevention mechanism which may be incorporated in the lens wash supply tubing 245c, upstream irrigation supply tubing 320, and/or downstream irrigation supply tubing 255c to help prevent backflow of water from either or both of the lens wash and irrigation tubing in the event of a negative pressure situation.

FIG. 12 illustrates an example water reservoir (e.g., container) 705. The water reservoir 705 may be similar in form and function to the water reservoirs 270, 305 of the systems 200, 300, described herein. For example, FIG. 12 illustrates that the water reservoir 705 may include an inner chamber designed to hold varying volumes of water 785. Additionally, FIG. 12 illustrates a cap 780 (e.g., a bottle cap) may be securely fastened to the water reservoir 705. Securement of the cap 780 to the water reservoir 705 may establish an air gap 775 between the cap 780 of the reservoir 705 and the water 785 in the reservoir 705.

FIG. 12 further illustrates a length of gas supply tubing 740 passing from one end positioned in an air gap 775 and through an opening in the cap 780 of the reservoir 705. It can be appreciated from FIG. 12 that the gas supply tubing 740 may be similar in form and function to the gas supply tubing 240c described herein. Additionally, FIG. 12 illustrates a length of lens wash tubing 745 having one end positioned within the water 785 of the reservoir 705 and passing through an opening in the cap 780 of the reservoir 705. It can be appreciated from FIG. 12 that the lens wash tubing 745 may be similar in form and function to the lens wash tubing 245c described herein. FIG. 12 further illustrates a length of irrigation tubing 755 having one end positioned within the water 785 of the reservoir 705 and passing through an opening in the cap 780 of the reservoir 705. It can be appreciated from FIG. 12 that the irrigation tubing 755 may be similar in form and function to the irrigation tubing 320 described herein. While FIG. 12 illustrates that the irrigation supply tubing 755 and lens wash tubing 745 may source water from the same reservoir 705, in some embodiments the irrigation water may be supplied via a pump (e.g., peristaltic pump) from a water source independent (not shown) from the water reservoir 705.

The detailed view of FIG. 12 further illustrates that endoscopic systems 200, 300 may include a ball check valve 770 positioned within the inner lumen of the lens wash tubing 745. As illustrated in FIG. 12, ball check valve 770 may include a ball 776 which is designed to sit (e.g., nest) within a shoulder 773 formed within the inner lumen of the lens wash tubing 745. The detailed view of FIG. 12 illustrates that the inner lumen of the lens wash tubing 745 includes a proximal inner lumen 772 (a proximal portion of the inner lumen of the lens wash tubing 745 which is proximal, or downstream, of the ball 776) and a distal inner lumen 774 (a distal portion of the inner lumen of the lens wash tubing 745 which is distal, or upstream, of the ball 776). The diameter $D_1$ of the proximal inner lumen 772 may be less than the diameter $D_2$ of the distal inner lumen 774. The shoulder 773 is formed as the inner lumen of the lens wash tubing 745 transitions from the proximal inner lumen 772 to the distal inner lumen 774.

FIG. 12 illustrates the ball check valve in a position in which the ball 776 is nested along the shoulder 773 of the lens wash tubing 745. In this position, the ball 776 prevents fluid from flowing back into the reservoir 705 from the endoscope 100. In some examples, the ball 776 may be made from a semi-compliant material which improves the ball's 776 ability to fit tightly along the shoulder 773, thereby sealing the ball 776 along the shoulder 773 and preventing fluid from flowing from the distal inner lumen 774 into the proximal inner lumen 772. In other examples, the ball 776 may be formed from a rigid material such as a metal (e.g., steel).

FIG. 13 illustrates water 785 being pressurized via the introduction of gas into the water reservoir 705 through the gas supply tubing 740. Referring back to the system configuration described with respect to FIG. 3C, when the endoscopic system 300 is in a lens wash delivery configuration, gas (pressure) may be delivered from the air pump 215 and out of the gas supply tubing 740 to the water reservoir 705. In FIG. 12, the gas entering the reservoir 705 is depicted by the arrow 764. The gas (pressure) pressurizes the surface of the water 785 in the reservoir 705 and pushes water up the lens wash supply tube 745. In FIG. 12, the water 585 flowing upstream through the lens wash tubing 745 is depicted by the arrows 762. The pressurized lens wash water 785 is pushed through the lens wash supply tube 745 upstream toward the endoscope 100. However, FIG. 12 further illustrates that water 785 flowing upstream through the lens wash tubing 745 may dislodge the ball 776 from the shoulder 773 of the lens wash tubing 745, thereby permitting the water 785 to flow around the ball 776 (e.g., from proximal inner lumen 772 and into the distal inner lumen 774) and upstream toward the endoscope 100.

A check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, or a flow check, among others.

Figure 14:
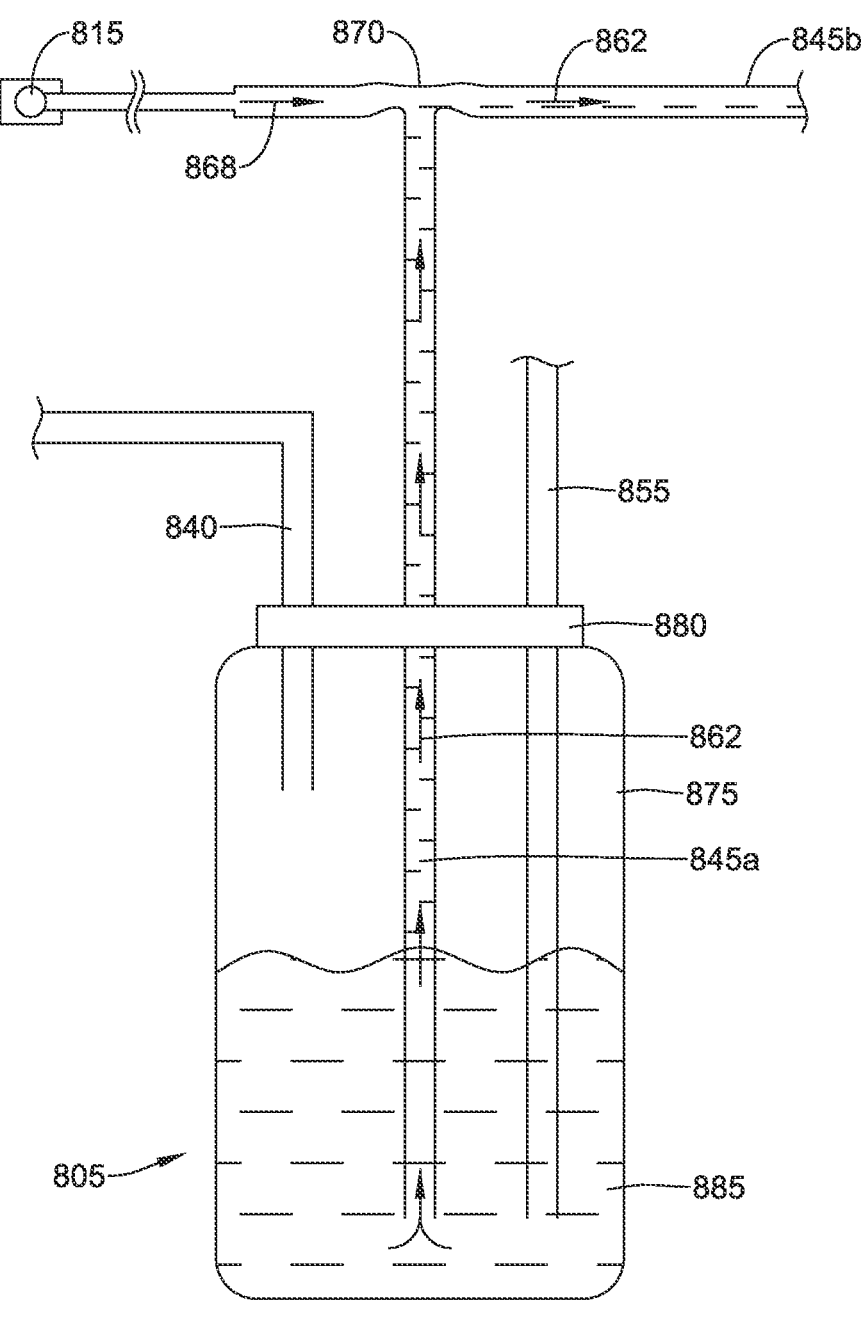
FIG. 14 depicts a portion of another endoscopic system including a container and a plurality of tubes coupled thereto, whereby the endoscopic system includes a siphon brake couple to one of the plurality of tubes.

FIG. 14 illustrates another backflow prevention mechanism which may be incorporated in the lens wash supply tubing 245c, upstream irrigation supply tubing 320, and/or downstream irrigation supply tubing 255c to help prevent backflow of water from either or both of the lens wash and irrigation tubing in the event of a negative pressure situation.

FIG. 14 illustrates an example water reservoir (e.g., container) 805. The water reservoir 805 may be similar in form and function to the water reservoirs 270, 305 of the systems 200, 300, described herein. For example, FIG. 14 illustrates that the water reservoir 805 may include an inner chamber designed to hold varying volumes of water 885. Additionally, FIG. 14 illustrates a cap 880 (e.g., a bottle cap) may be securely fastened to the water reservoir 805. Securement of the cap 880 to the water reservoir 805 may establish an air gap 875 between the cap 880 of the reservoir 805 and the water 885 in the reservoir 805.

FIG. 14 further illustrates a length of gas supply tubing 840 passing from one end positioned in an air gap 875 and through an opening in the cap 880 of the reservoir 805. It can be appreciated from FIG. 8 that the gas supply tubing 840 may be similar in form and function to the gas supply tubing 240c described herein. Additionally, FIG. 14 illustrates a length of downstream lens wash tubing 845a having one end positioned within the water 885 of the reservoir 805 and passing through an opening in the cap 880 of the reservoir 805. It can be appreciated from FIG. 14 that the downstream lens wash tubing 845a may be similar in form and function to the lens wash tubing 245c described herein. FIG. 14 further illustrates a length of irrigation tubing 855 having one end positioned within the water 885 of the reservoir 805 and passing through an opening in the cap 880 of the reservoir 805. It can be appreciated from FIG. 14 that the irrigation tubing 855 may be similar in form and function to the irrigation tubing 320 described herein. While FIG. 14 illustrates that the irrigation supply tubing 855 and lens wash tubing 845 may source water from the same reservoir 805, in some embodiments the irrigation water may be supplied via a pump (e.g., peristaltic pump) from a water source independent (not shown) from the water reservoir 805.

FIG. 14 further illustrates that endoscopic systems 200, 300 may include a siphon break 870. The siphon break 870 may include a first inlet coupled to the downstream lens wash tubing 845a and an outlet which is coupled to a first end of an upstream lens wash tubing 845b. Further, a second end (opposite the first end) of the upstream lens wash tubing 845b may be coupled to an inlet of the endoscope 100. In other words, the siphon break 870 may be positioned in fluid communication with both the downstream lens wash tubing 845a and the upstream lens wash tubing 845b, whereby fluid drawn from the water reservoir 805 may pass through the downstream lens washing 845a, pass through a portion of the siphon break 870 and then pass into the upstream lens wash tubing 845b toward the endoscope 100.

FIG. 14 further illustrates that the siphon break 870 may also include an inlet coupled to an air pump 815. The air pump 815 may be designed to provide an air stream (depicted by the arrow 868 in FIG. 14) traveling from the pump 815 into the siphon break 870, whereby the air stream may effectively pull the water 885 up the downstream lens wash tubing 845a by imparting a venturi effect. The direction of the water 885 being pulled up from the water reservoir 805 is depicted by the arrows 862 in FIG. 14. However, it can be appreciated that the siphon break may also close upon in response to the flow of fluid from be fluid reservoir 805.

Figure 15:
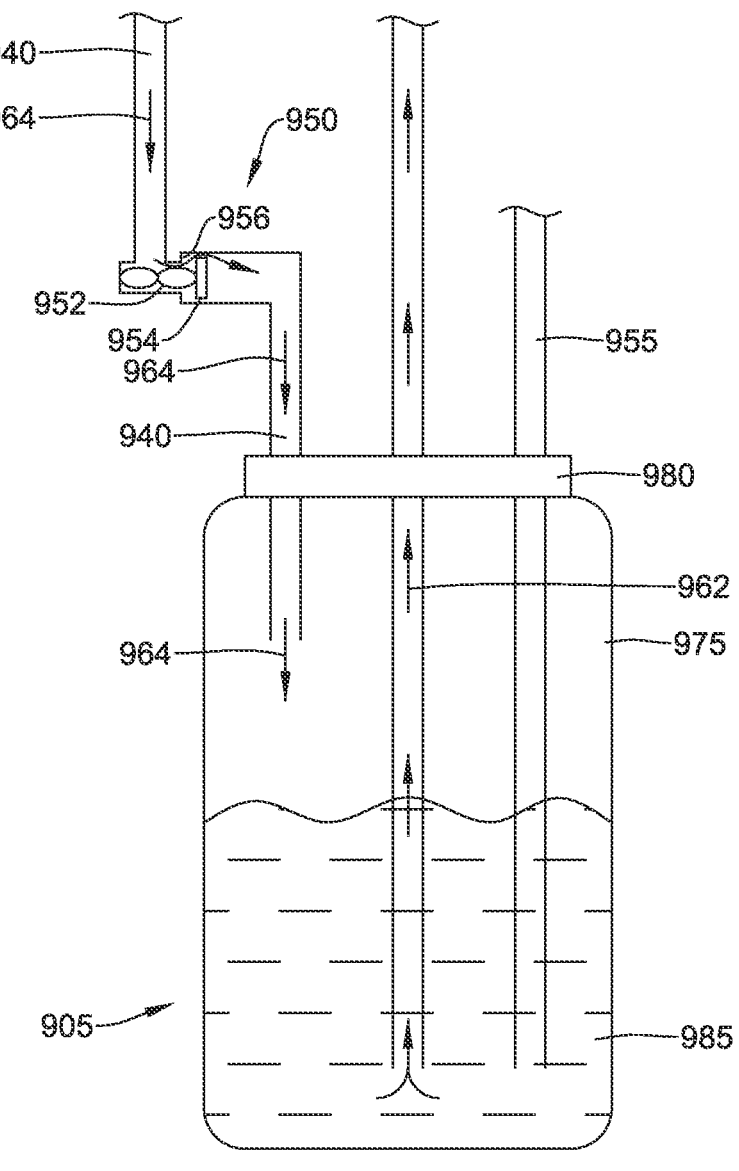
FIG. 15 depicts a portion of another endoscopic system including a container and a plurality of tubes coupled thereto, whereby endoscopic system includes an air flow regulator couple to one of the plurality of tubes.
Figure 16:
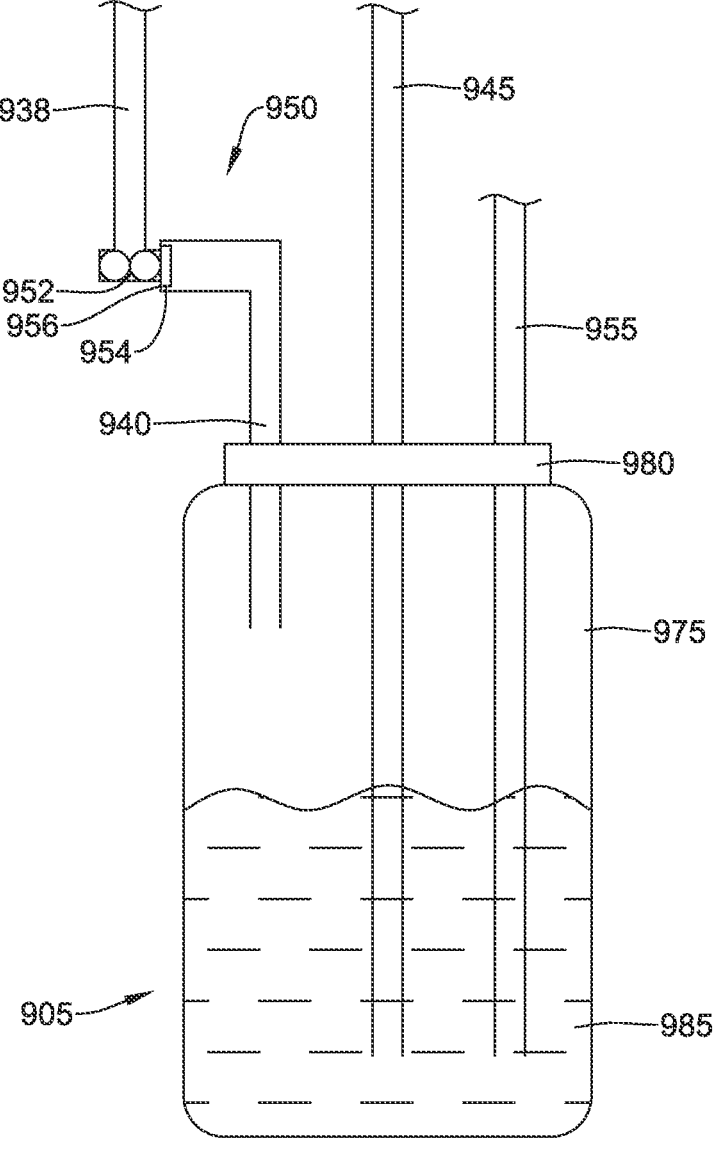
FIG. 16 depicts the container and the plurality of tubes of FIG. 15, whereby gas is prevented from passing back through the air flow regulator of FIG. 15.

FIGS. 15-16 illustrate another backflow prevention mechanism which may be incorporated in the gas supply tubing 240c, lens wash supply tubing 245c, upstream irrigation supply tubing 320, and/or downstream irrigation supply tubing 255c to help prevent backflow of water from either or both of the lens wash and irrigation tubing in the event of a negative pressure situation.

FIG. 15 illustrates an example water reservoir (e.g., container) 905. The water reservoir 905 may be similar in form and function to the water reservoirs 270, 305 of the systems 200, 300, described herein. For example, FIG. 15 illustrates that the water reservoir 905 may include an inner chamber designed to hold varying volumes of water 985. Additionally, FIG. 15 illustrates a cap 980 (e.g., a bottle cap) may be securely fastened to the water reservoir 905. Securement of the cap 980 to the water reservoir 905 may establish an air gap 975 between the cap 980 of the reservoir 905 and the water 985 in the reservoir 905.

FIG. 15 further illustrates a length of lens wash tubing 945 having one end positioned within the water 985 of the reservoir 905 and passing through an opening in the cap 980 of the reservoir 905. It can be appreciated from FIG. 15 that the lens wash tubing 945 may be similar in form and function to the lens wash tubing 245c described herein. FIG. 15 further illustrates a length of irrigation tubing 955 having one end positioned within the water 985 of the reservoir 905 and passing through an opening in the cap 980 of the reservoir 905. It can be appreciated from FIG. 15 that the irrigation tubing 955 may be similar in form and function to the irrigation tubing 320 described herein. While FIG. 15 illustrates that the irrigation supply tubing 955 and lens wash tubing 945 may source water from the same reservoir 905, in some embodiments the irrigation water may be supplied via a pump (e.g., peristaltic pump) from a water source independent (not shown) from the water reservoir 905.

FIG. 15 further illustrates a length of gas supply tubing 940 passing from one end positioned in the air gap 975 and through an opening in the cap 980 of the reservoir 905. It can be appreciated from FIG. 15 that the gas supply tubing 940 may be similar in form and function to the gas supply tubing 240c described herein.

FIG. 15 further illustrates that endoscopic systems 200, 300 may further include a gas flow and pressure regulator 950 (e.g., in-flow check valve, in-flow control valve, etc.) may be disposed in the path of the gas supply tubing 940 to maintain a small positive pressure in the water reservoir 905. In other words, pressure built within the water reservoir 905 may create a pressure difference between the water 985 and the gas supply tubing 905 which helps to maintain a positive pressure inside the water reservoir 905, even when large amounts of water may be removed from the water reservoir 905 when a user is utilizing the irrigation function. This arrangement compensates for any time lag in air being delivered from the air pump 215 to the water reservoir 905 which might otherwise cause a negative pressure vacuum in the water reservoir 905.

FIG. 15 illustrates that the flow regulator 950 may include a valve pad 954 attached to a first end of a spring 952. FIG. 15 further illustrates that a second end of the spring 952 may be fixedly attached to an inner wall surface of the flow regulator 950. Accordingly, the spring 952 may be permitted to expand and contract within an inner chamber of the flow regulator 950. Additionally, FIG. 15 illustrates that the flow regulator 950 may further include a shoulder 956 which may provide a surface upon which the valve pad 954 may contact when the spring 952 is contracted. In other words, the shoulder 956 may act as a positive stop for the valve pad 954 when the spring 952 is contracted within the inner chamber of the pressure regulator 950.

Referring back to the system configuration described with respect to FIG. 3C, when the endoscopic system 300 is in a lens wash delivery configuration, gas (pressure) may be delivered from the air pump 215 and through the gas supply tubing 940 to the water reservoir 905. Further, when gas is passed downstream through the gas supply tubing 940 and enters the flow regulator 950 (as shown by arrows 964 in FIG. 15), the gas may force the spring 952 to expand, thereby permitting the gas to flow around the valve pad 954 and downstream through the regulator 950 and into the water reservoir 905. As the gas is introduced into the water reservoir 905 through the gas supply tubing 940, the gas (pressure) pressurizes the surface of the water 985 in the reservoir 905 and pushes water up the lens wash supply tube 945. The pressurized lens wash water 985 is pushed through the lens wash supply tube 945 to the endoscope 100.

However, FIG. 16 illustrates that after the air pump 215 stops delivering gas pressure through the gas supply tubing 940 (and thereby forcing the spring 952 to expand), the spring 952 of the flow regulator 950 may contract (e.g., relax), thereby allowing the valve pad 954 to seal against the shoulder 956 of the pressure regulator 950. As discussed herein, permitting the valve pad 954 to seal against the shoulder 956 of the flow regulator 950 may maintain pressure built within the water reservoir 905 and create a pressure difference between the water 985 and the gas supply tubing 905 which helps to maintain a positive pressure inside the water reservoir 905, even when large amounts of water may be removed from the water reservoir 905 when a user is utilizing the irrigation function. This arrangement compensates for any time lag in air being delivered from the air pump 215 to the water reservoir 905 which might otherwise cause a negative pressure vacuum in the water reservoir 905.

It can be further appreciated that a variety of check valves, including one or more check valves disclosed herein, may function as a flow regulator in a similar manner to the flow regulator 950. For example, a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, or a flow check, among others may be utilized as a flow regular to create a pressure difference between the water 985 and the gas supply tubing 905, thereby helping maintain a positive pressure inside the water reservoir 905.

Figure 17:
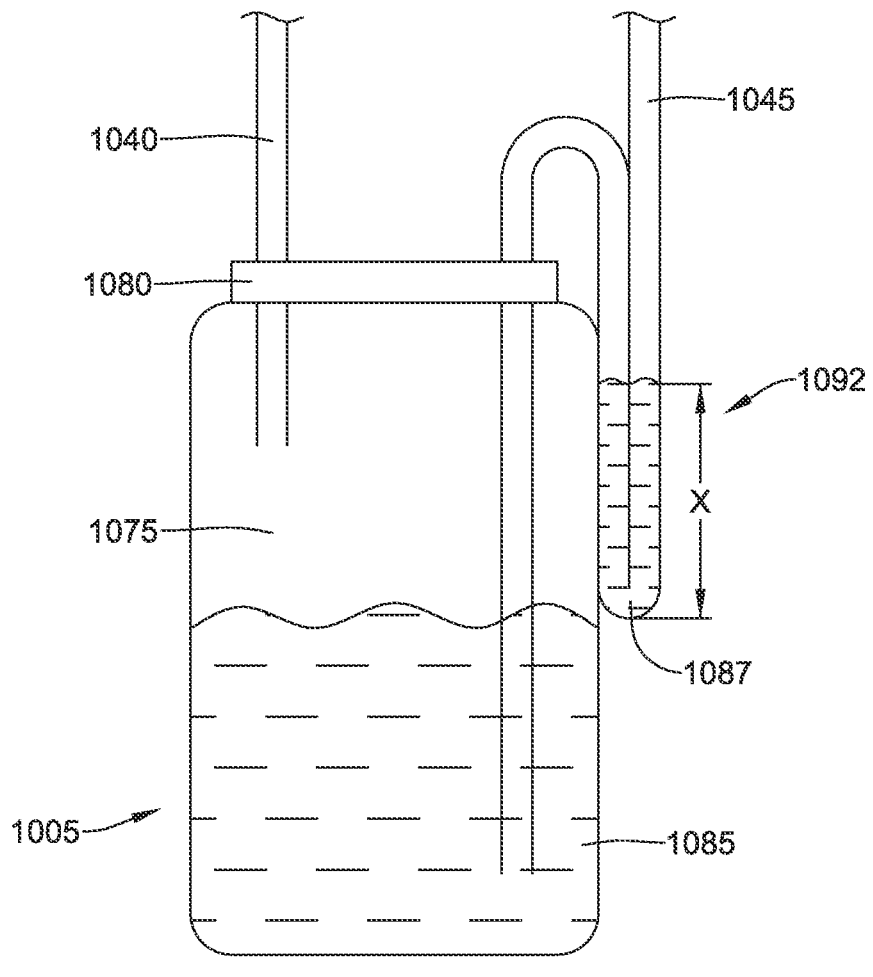
FIG. 17 depicts a portion of another endoscopic system including a container and a plurality of tubes coupled thereto, whereby one of the tubes includes a s-trap.

FIG. 17 illustrates another backflow prevention mechanism which may be incorporated in the lens wash supply tubing 245c, upstream irrigation supply tubing 320, and/or downstream irrigation supply tubing 255c to help prevent backflow of water from either or both of the lens wash and irrigation tubing in the event of a negative pressure situation.

FIG. 17 illustrates an example water reservoir (e.g., container) 1005. The water reservoir 1005 may be similar in form and function to the water reservoirs 270, 305 of the systems 200, 300, described herein. For example, FIG. 17 illustrates that the water reservoir 1005 may include an inner chamber designed to hold varying volumes of water 1085. Additionally, FIG. 17 illustrates a cap 1080 (e.g., a bottle cap) may be securely fastened to the water reservoir 1005. Securement of the cap 1080 to the water reservoir 1005 may establish an air gap 1075 between the cap 1080 of the reservoir 1005 and the water 1085 in the reservoir 1005.

FIG. 17 further illustrates a length of gas supply tubing 1040 passing from one end positioned in an air gap 1075 and through an opening in the cap 1080 of the reservoir 1005. It can be appreciated from FIG. 17 that the gas supply tubing 1040 may be similar in form and function to the gas supply tubing 240c described herein. Additionally, FIG. 17 illustrates a length of lens wash tubing 1045 having one end positioned within the water 1085 of the reservoir 1005 and passing through an opening in the cap 1080 of the reservoir 505. It can be appreciated from FIG. 8 that the lens wash tubing 1045 may be similar in form and function to the lens wash tubing 245c described herein.

FIG. 17 further illustrates that the lens wash tubing 1045 may be formed to into an undulated configuration 1092 in which the lens wash tubing 1045, after passing through the cap 1080, folds over (e.g., bends around, wraps over, folds back) and extends downward along the outer surface of the water reservoir 1005. After extending a given length along the outer surface of the water reservoir 1005, the lens wash tubing 1045 may fold back on itself and extend upward to form the undulating portion 1092. Additionally, FIG. 17 further illustrates that a column of water 1087 may be placed within the lens wash tubing 1045 and extend along both the downward and upward portion of the lens wash tubing 1045. The column of water 1087 positioned within the lens wash tubing 1045 of FIG. 17 generally forms a "U" shape having a vertical column height "X."

The water 1087 present in the lens wash tubing 1045 may prevent static fluid present in the lens wash tubing 1045 from flowing back from the endoscope 100 and back into the reservoir 1005. In other words, any static fluid present in the endoscope 100 that travels back through the lens wash tubing 1045 would have to overcome the pressure created by the body of still water 1087 present in the undulating portion 1092 to make its way back into the water reservoir 1005.

In some examples, the undulating configuration 1092 may be included in a variety of tubing and structures of the endoscopic systems 200, 300. For example, the undulating configuration 1092 illustrated in FIG. 17 may be integrated into the design of the water reservoir 1005. In other words, a portion of the wall defining the water reservoir 1005 could define the undulating configuration 1092 illustrated in FIG. 17, whereby the lens wash tubing 1045 may connect directly to that portion of the water reservoir 1005.

Figure 18:
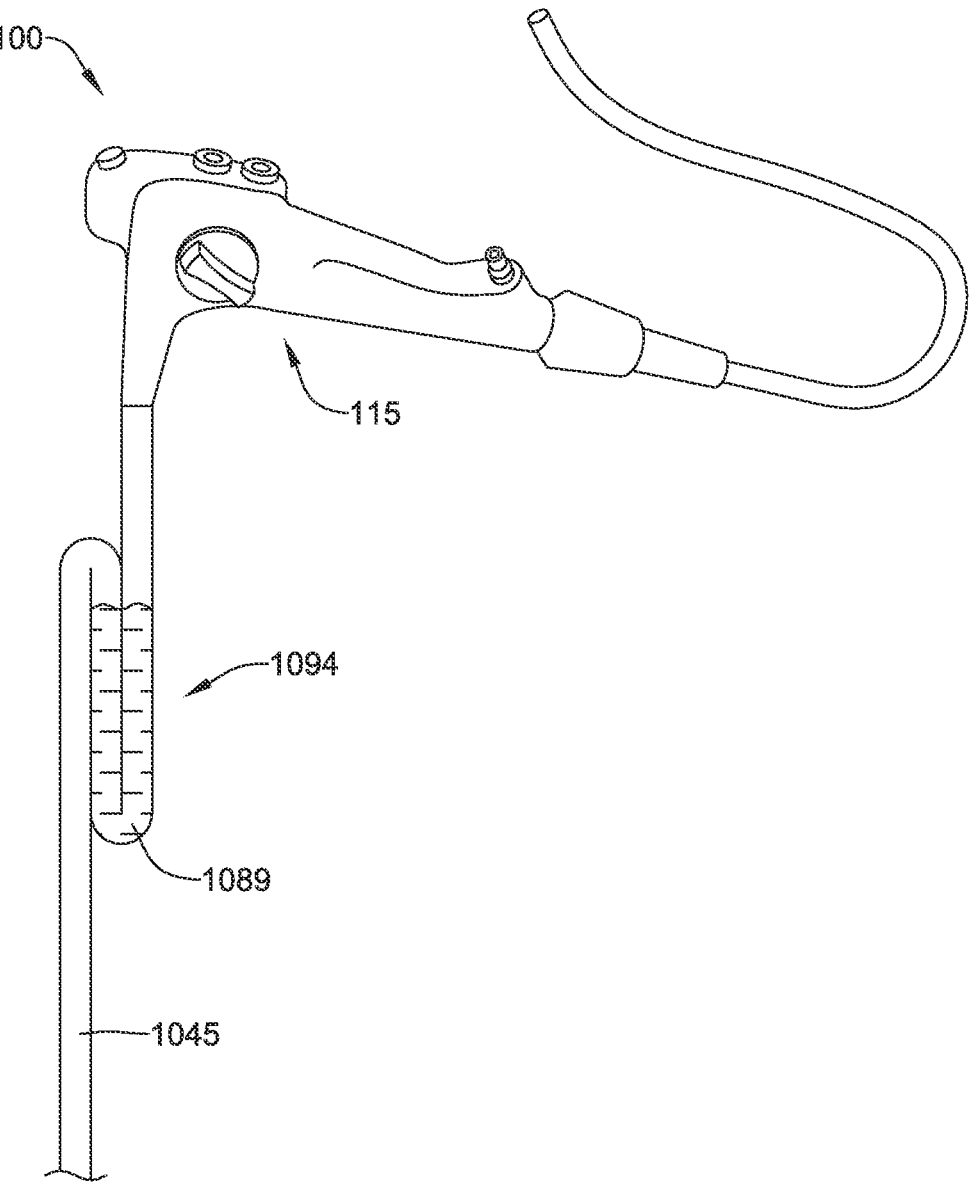
FIG. 18 depicts an endoscope and a tube connected thereto, whereby the tube includes a s-trap.

Additionally, FIG. 18 is a highly simplified schematic drawing which illustrates that, in some examples, the undulating configuration 1092 in the lens wash tubing 1045 of FIG. 17 may be positioned adjacent to the operating handle 115 of the endoscope 100. For example, as shown in FIG. 18, the undulating configuration 1092 may include a vertical column of water 1089, similar to that describe above wither respect to the undulating configuration 1092 shown in FIG. 17.

Figures 19, 20, 21:
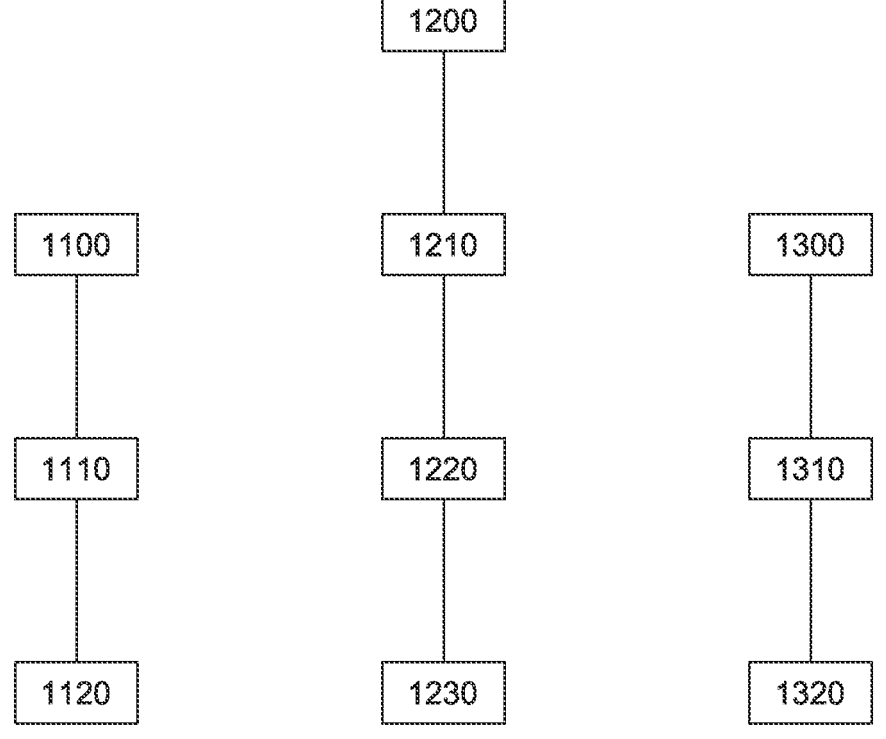
FIG. 19 is a flow chart depicting an example method.
FIG. 20 is a flow chart depicting an example method.
FIG. 21 is a flow chart depicting an example method.

FIG. 19 is a flowchart depicting an example method. The method may describe a possible flow within the hybrid system 300. For example, when gas is called for at the distal tip 100c, for example, to clean the end face 100d of the distal tip or insufflate the patient body in the treatment area, the user may close off the vent hole in the gas/water valve 140 with a thumb, finger, or the like (first position) as represented by box 1100. The gas (pressure) may be delivered along from the air pump 215 and flowed through the gas feed line 240b in the umbilical 260 via the connector portion 265 as represented by box 1110. The gas may continue through the gas/water valve 140 to the gas supply line 240a in the endoscope shaft 100a and out the gas/lens wash nozzle 220 at the distal tip 100c as represented by box 1120.

FIG. 20 is a flowchart depicting an example method. The method may describe a possible flow within the hybrid system 300. For example, when lens wash is called for at the distal tip 100c, for example, to clean the end face 100d of the distal tip 100c, the user, keeping the vent hole in the air/water valve closed off, depresses the valve 140 to its furthest point in the valve well 135 as represented by box 1200. The second position blocks off the gas supply to both atmosphere and the gas supply line 240a in the endoscope, and opens up the gas/water valve 140 to allow lens wash water to pass through to the lens wash supply line 245a in the endoscope shaft 100a and out the gas/lens wash nozzle 220 at the distal tip 100c as represented by box 1210. In this state, gas (pressure) is delivered along path C from the air pump 215, through the branched line in the connector portion 265 and out of the gas supply tubing 240c to the water reservoir 305 as represented by box 1220. The gas (pressure) pressurizes the surface of the remaining water 285 in the reservoir 305 and pushes water up the lens wash supply tube 245c, through the lens wash feed line 245b in the umbilical 260 and through the gas/water valve 140 as represented by box 1230.

FIG. 21 is a flowchart depicting an example method. The method may describe a possible flow within the hybrid system 300. For example, when irrigation is called for at the distal tip 100c, for example, if visibility in the treatment area is poor or blocked by debris, or the like, the user activates the irrigation pump 315 (e.g., by depressing foot switch 318) to delivery water along path D as represented by box 1300. With the pump 315 activated, water is sucked out of the water reservoir 305 through the upstream irrigation supply tubing 320 and pumped along the downstream irrigation supply tubing 255c to the connector portion 265 as represented by box 1310. The irrigation pump head pressure pushes the irrigation water further through the irrigation feed line 255*b* in the umbilical 260, through the irrigation supply line 255*a* in the endoscope shaft 100*a*, and out the irrigation opening 225 at the distal tip 100*c* as represented by box 1320.

It can be further appreciated that the backflow prevention mechanisms described herein may be applied to any of the tubes of system 200, 300. For example, the backflow prevention mechanisms may be incorporated in one or more of the gas supply tubing, lens wash supply tubing, upstream irrigation supply tubing, downstream irrigation supply tubing or any other tubing or component of system 200, 300 to help prevent backflow of water from either or both of the lens wash and irrigation tubing in the event of a negative pressure situation.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. A fluid reservoir and tube set arranged and configured to couple to an endoscope for use in an endoscopic procedure, the fluid reservoir and tube set comprising:
    a fluid reservoir configured to contain a fluid;
    a fluid supply tube configured to be coupled to the endoscope and having a lumen extending therethrough, wherein the lumen is in fluid communication with the fluid reservoir; and
    a first backflow prevention mechanism coupled to the fluid supply tube, the first backflow prevention mechanism configured to permit fluid to flow through the fluid supply tube from the fluid reservoir to the endoscope and to prevent fluid from flowing back through the fluid supply tube from the endoscope to the fluid reservoir, wherein the first backflow prevention mechanism includes a clamp positioned adjacent to the fluid supply tube.

2. The fluid reservoir and tube set of claim 1, wherein the fluid supply tube is configured to permit fluid to flow from the fluid reservoir to a lens of the endoscope.

3. The fluid reservoir and tube set of claim 1, wherein the first backflow prevention mechanism further includes a portion of the fluid supply tube, wherein the portion of the fluid supply tube is configured to shift between a radially closed configuration and a radially open configuration.

4. The fluid reservoir and tube set of claim 3, wherein when in the closed configuration, the portion of the fluid supply tube is configured to prevent fluid from flowing through the fluid supply tube from the endoscope to the fluid reservoir.

5. The fluid reservoir and tube set of claim 4, further comprising a gas supply tube, the gas supply tube including a first end and a second end, the first end configured to be coupled to a gas pump, and the second end positioned within the fluid reservoir, and wherein the gas supply tube is configured to permit gas to flow into and pressurize the fluid in the fluid reservoir.

6. The fluid reservoir and tube set of claim 5, wherein the portion of the fluid supply tube is configured to shift from the closed configuration to the open configuration in response to the pressurized fluid flowing through the fluid supply tube.

7. The fluid reservoir and tube set of claim 3, wherein the portion of the fluid supply tube includes an elongate cross-sectional shape in the closed configuration.

8. The fluid reservoir and tube set of claim 3, wherein the portion of the fluid supply tube includes a circular cross-sectional shape in the closed configuration.

9. The fluid reservoir and tube set of claim 1, wherein the first backflow prevention mechanism further includes an elastic section of material.

10. The fluid reservoir and tube set of claim 1, wherein the clamp is configured to squeeze the fluid supply tube to prevent from flowing back through the fluid supply tube from the endoscope to the fluid reservoir.

11. The fluid reservoir and tube set of claim 10, wherein the clamp is configured to open in response to pressurized fluid flowing through the fluid supply tube.

12. The fluid reservoir and tube set of claim 11, wherein the clamp is attached to the fluid reservoir.

13. The fluid reservoir and tube set of claim 1, further comprising an irrigation supply tube including a first end, a second end, and a lumen extending therethrough, the lumen of the irrigation supply tube being in fluid communication with the fluid reservoir.

14. The fluid reservoir and tube set of claim 13, further comprising a second backflow prevention mechanism coupled to the irrigation supply tube, the second backflow prevention mechanism configured to permit fluid to flow through the irrigation supply tube from the fluid reservoir to the endoscope, and to prevent fluid from flowing back through the irrigation supply tube from the endoscope to the fluid reservoir.

* * * * *